United States Patent
Yankelevitz et al.

(10) Patent No.: US 7,876,939 B2
(45) Date of Patent: Jan. 25, 2011

(54) MEDICAL IMAGING SYSTEM FOR ACCURATE MEASUREMENT EVALUATION OF CHANGES IN A TARGET LESION

(75) Inventors: David F. Yankelevitz, Brooklyn, NY (US); Anthony P. Reeves, Ithaca, NY (US); Claudia Ingrid Henschke, New York, NY (US)

(73) Assignee: David Yankelevitz, Brooklyn, NY (US)

( * ) Notice: Subject to any disclaimer, the term of this patent is extended or adjusted under 35 U.S.C. 154(b) by 1099 days.

(21) Appl. No.: 11/552,516

(22) Filed: Oct. 24, 2006

(65) Prior Publication Data

US 2007/0100226 A1 May 3, 2007

Related U.S. Application Data

(63) Continuation-in-part of application No. PCT/US2005/013968, filed on Apr. 25, 2005.

(60) Provisional application No. 60/565,327, filed on Apr. 26, 2004.

(51) Int. Cl.
*G06K 9/00* (2006.01)
(52) U.S. Cl. ...................... 382/128; 382/131; 382/173; 382/294; 382/156
(58) Field of Classification Search ................. 382/128, 382/131, 195; 600/407
See application file for complete search history.

(56) References Cited

U.S. PATENT DOCUMENTS

| | | |
|---|---|---|
| 4,856,528 A | 8/1989 | Yang et al. |
| 5,917,929 A | 6/1999 | Marshall et al. |
| 6,014,452 A | 1/2000 | Zhang et al. |
| 6,035,056 A | 3/2000 | Karssemeijer |
| 6,075,879 A | 6/2000 | Roehrig et al. |
| 6,198,838 B1 | 3/2001 | Roehrig et al. |
| 6,263,092 B1 | 7/2001 | Roehrig et al. |

(Continued)

FOREIGN PATENT DOCUMENTS

WO    WO 01/78005    10/2001

OTHER PUBLICATIONS

Mullally et al., "Segmentation of nodules on chest computed tomography for growth assessment," Medical Physics, AIP, Melville, NY, US, vol. 31, No. 4, Apr. 1, 2004, pp. 839-848.*

(Continued)

*Primary Examiner*—Brian Casler
*Assistant Examiner*—John F Ramirez
(74) *Attorney, Agent, or Firm*—Citadel Patent Law; George A. Leone

(57) ABSTRACT

A body part is scanned to produce a first set of imaging data. A target lesion in the imaging data is identified. The body part is rescanned at a subsequent time so as to produce a second set of imaging data. The target lesion is identified in the second set of imaging data and the size of the target lesion is measured in the first and second sets of imaging data to determine two apparent image volumes corresponding to the first and second sets of imaging data. A change in size is estimated by comparing the first and second apparent lesion sizes. A variance on the change in size is estimated so as to determine a bound on the change in size measurement.

21 Claims, 26 Drawing Sheets

U.S. PATENT DOCUMENTS

| | | |
|---|---|---|
| 6,301,378 B1 | 10/2001 | Karssemeijer et al. |
| 6,404,908 B1 | 6/2002 | Schneider et al. |
| 6,580,818 B2 | 6/2003 | Karssemeijer |
| 6,640,001 B2 | 10/2003 | Roehrig et al. |
| 6,766,043 B2 | 7/2004 | Zeng |
| 6,909,794 B2 * | 6/2005 | Caspi ............... 382/128 |
| 6,909,795 B2 | 6/2005 | Tecotzky et al. |
| 6,909,797 B2 | 6/2005 | Romsdahl et al. |
| 6,925,200 B2 | 8/2005 | Wood et al. |
| 7,054,473 B1 | 5/2006 | Roehrig et al. |
| 2002/0159622 A1 | 10/2002 | Schneider |
| 2003/0016850 A1 * | 1/2003 | Kaufman et al. ......... 382/128 |
| 2003/0095696 A1 | 5/2003 | Reeves |
| 2004/0184647 A1 | 9/2004 | Reeves |
| 2004/0252870 A1 | 12/2004 | Reeves |
| 2005/0013471 A1 | 1/2005 | Snoeren et al. |
| 2005/0163360 A1 | 7/2005 | Snoeren et al. |
| 2006/0147099 A1 | 7/2006 | Marshall |
| 2006/0239544 A1 | 10/2006 | Yankelevitz |

OTHER PUBLICATIONS

R2 Technology, Inc., What is CAD?, 2004.

University of Virginia School of Medicine, Lines and Tubes, 1999.

National Cancer Institute, Improving Methods for Breast Cancer Detection and Diagnosis, Apr. 26, 2002.

Ginneken, Computer-Aided Diagnosis in Chest Radiography: A Survey, IEEE Transactions on Medical Imaging, vol. 20, No. 12, Dec. 2001.

Swensen, MD et al., Scanlon Symposium-Lung Cancer, Mar. 12, 2000.

Therasse, P. et al., New Guidelines to Evaluate the Response to Treatment in Solid Tumors, Journal of the National Cancer Institute, vol. 92, No. 3, Feb. 2, 2000.

Ettinger et al., "Computed tomography assisted volumetric measure of response to therapy," Am. J. Ciin. Oncol., vol. 8, 1985, pp. 413-418.

Mullally et al., "Segmentation of nodules on chest computed tomography for growth assessment," Medical Physics, AIP, Melville, NY, US, vol. 31, No. 4, Apr. 1, 2004, pp. 839-848.

* cited by examiner

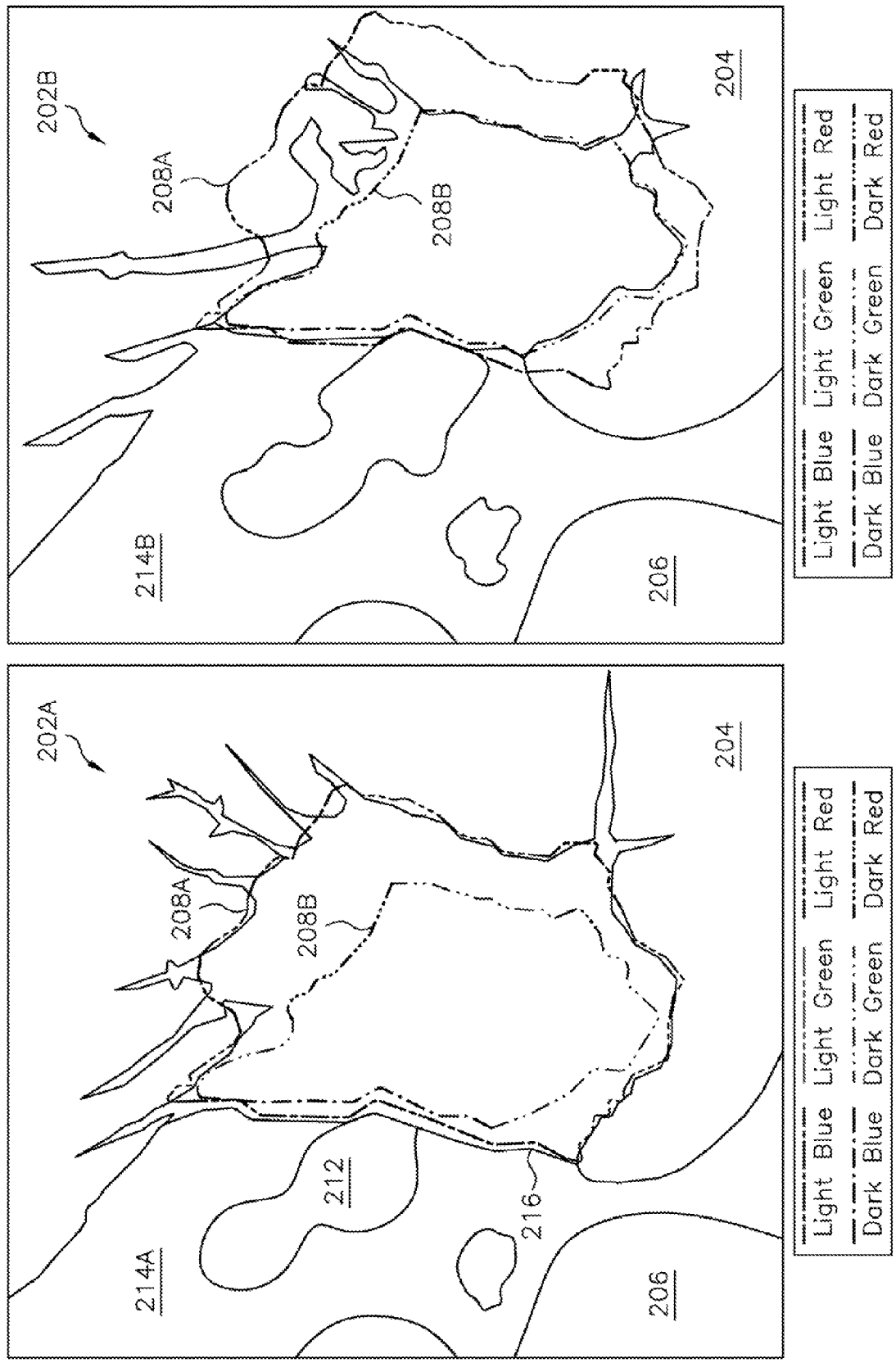

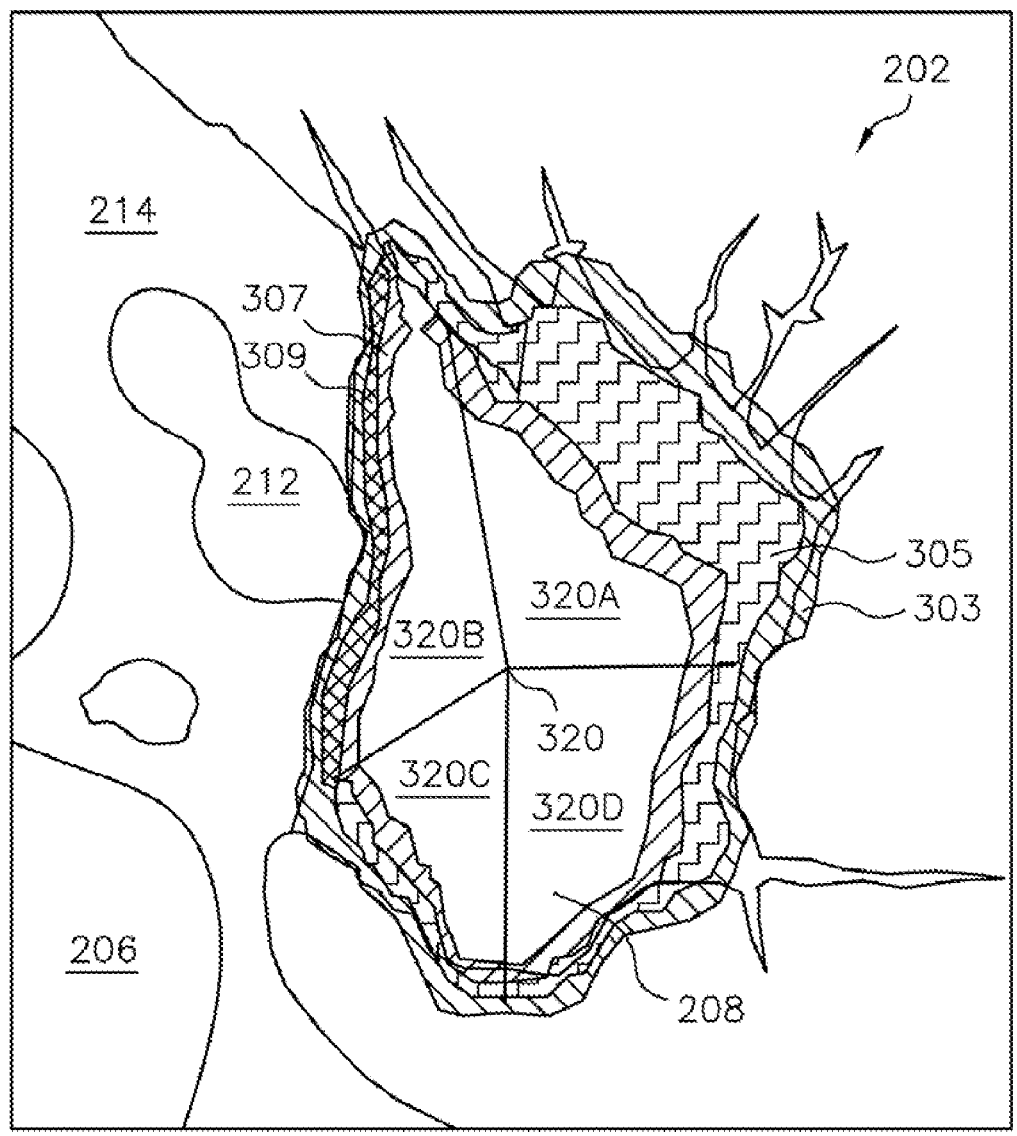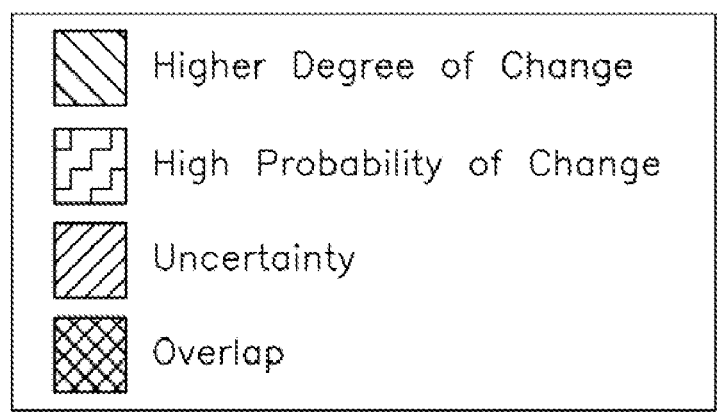
FIG. 10

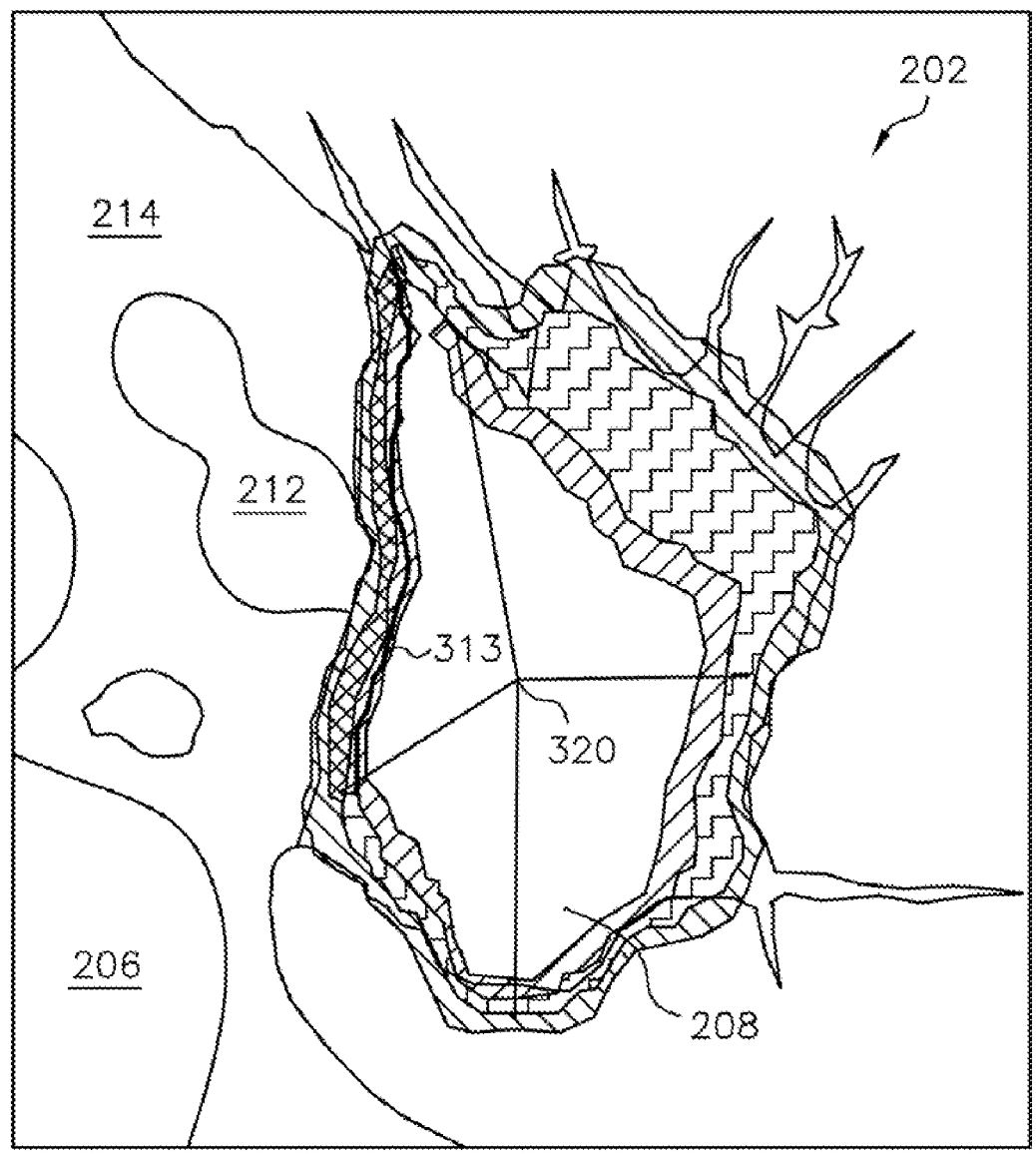
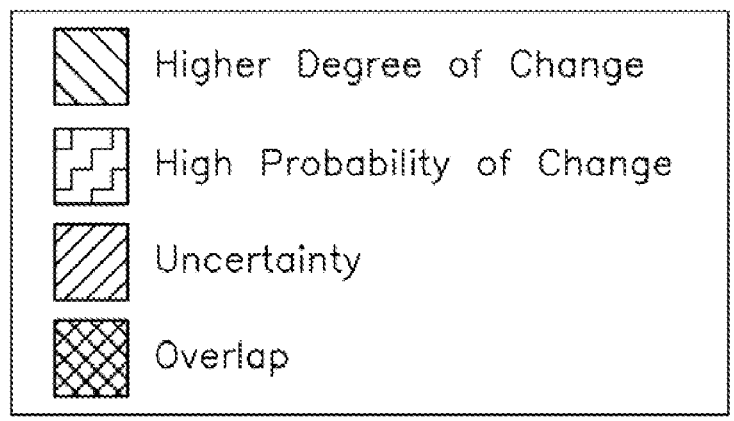
FIG. 11

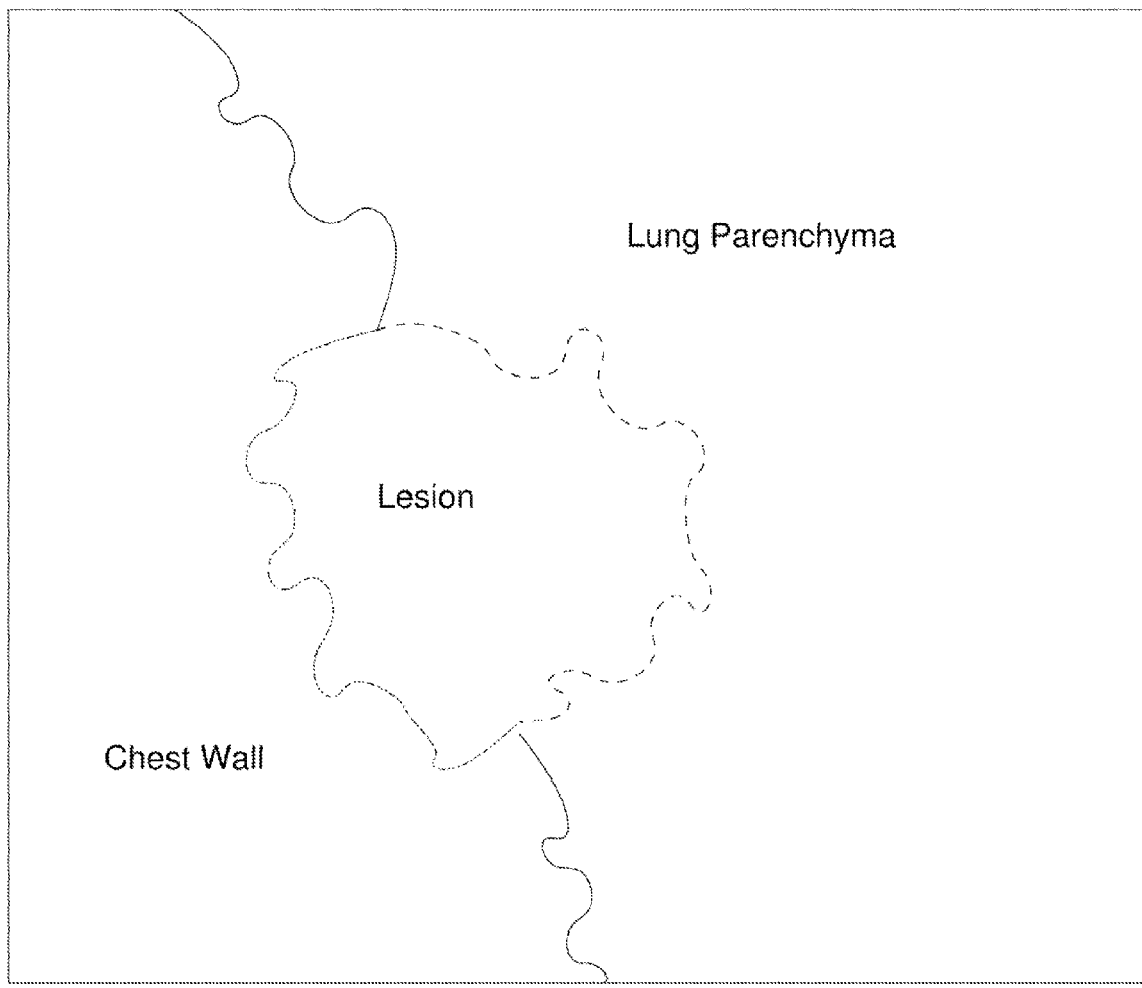
Figure 12 A, Original Image

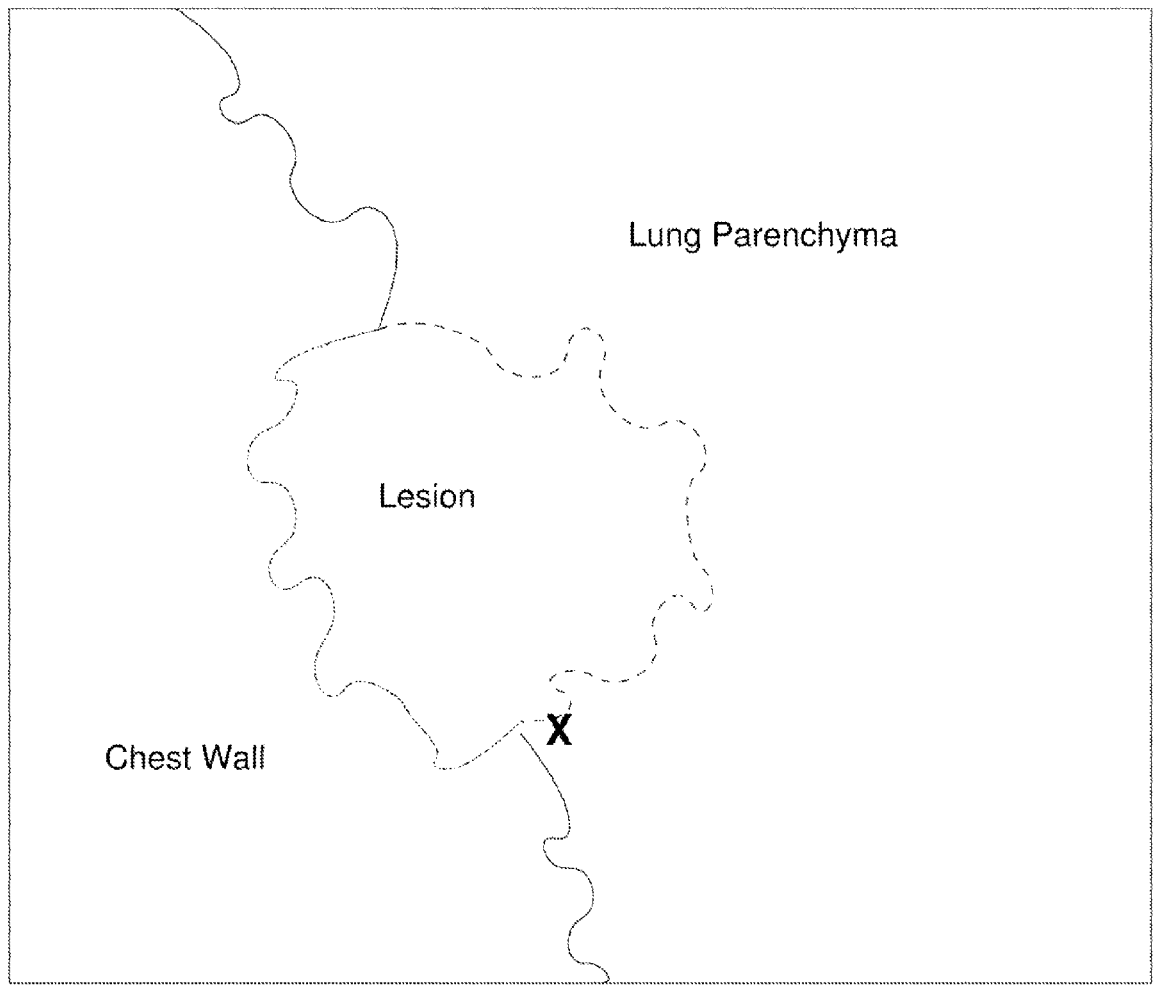
Figure 12 B, User marks initial point

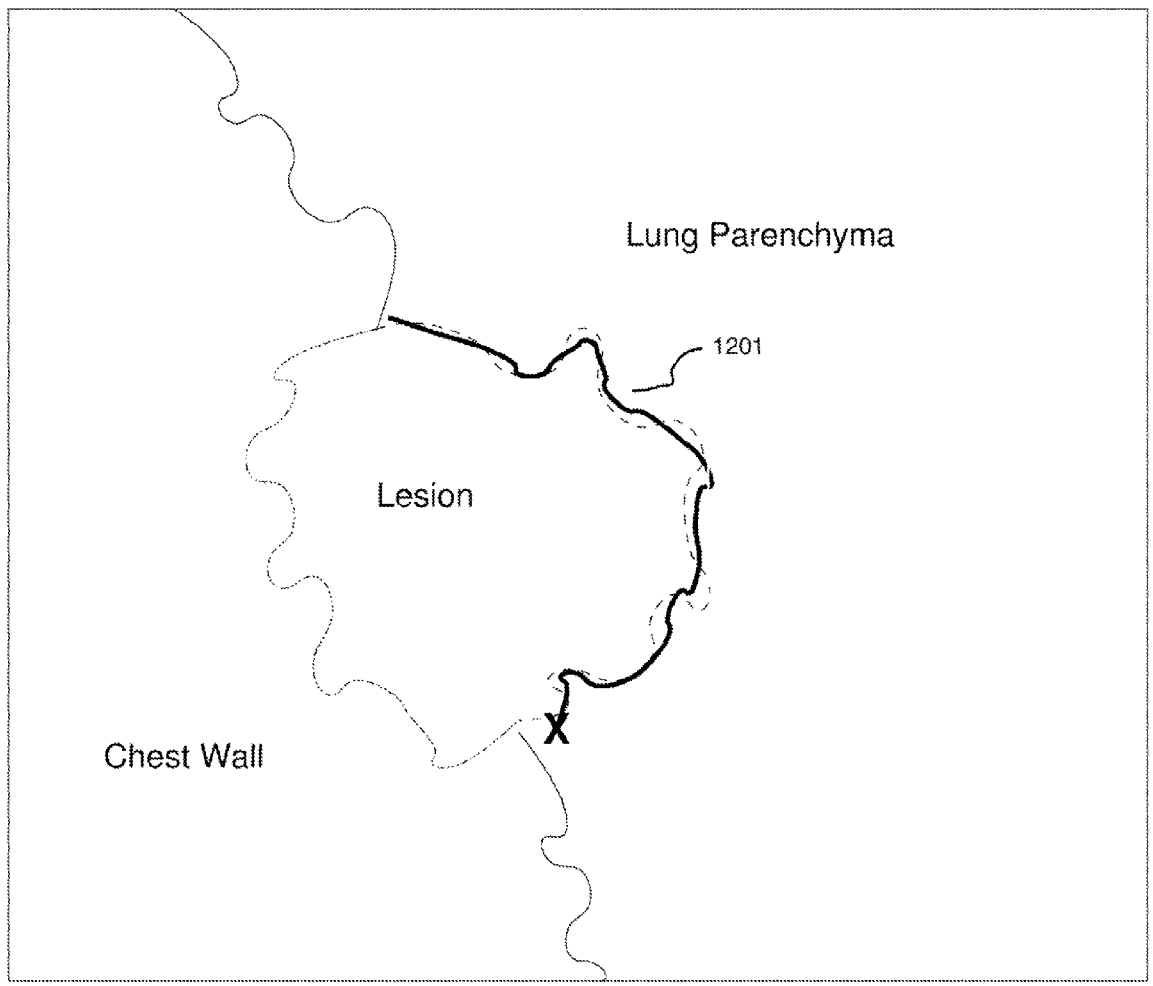
Figure 12 C, Computer marks well defined boundary

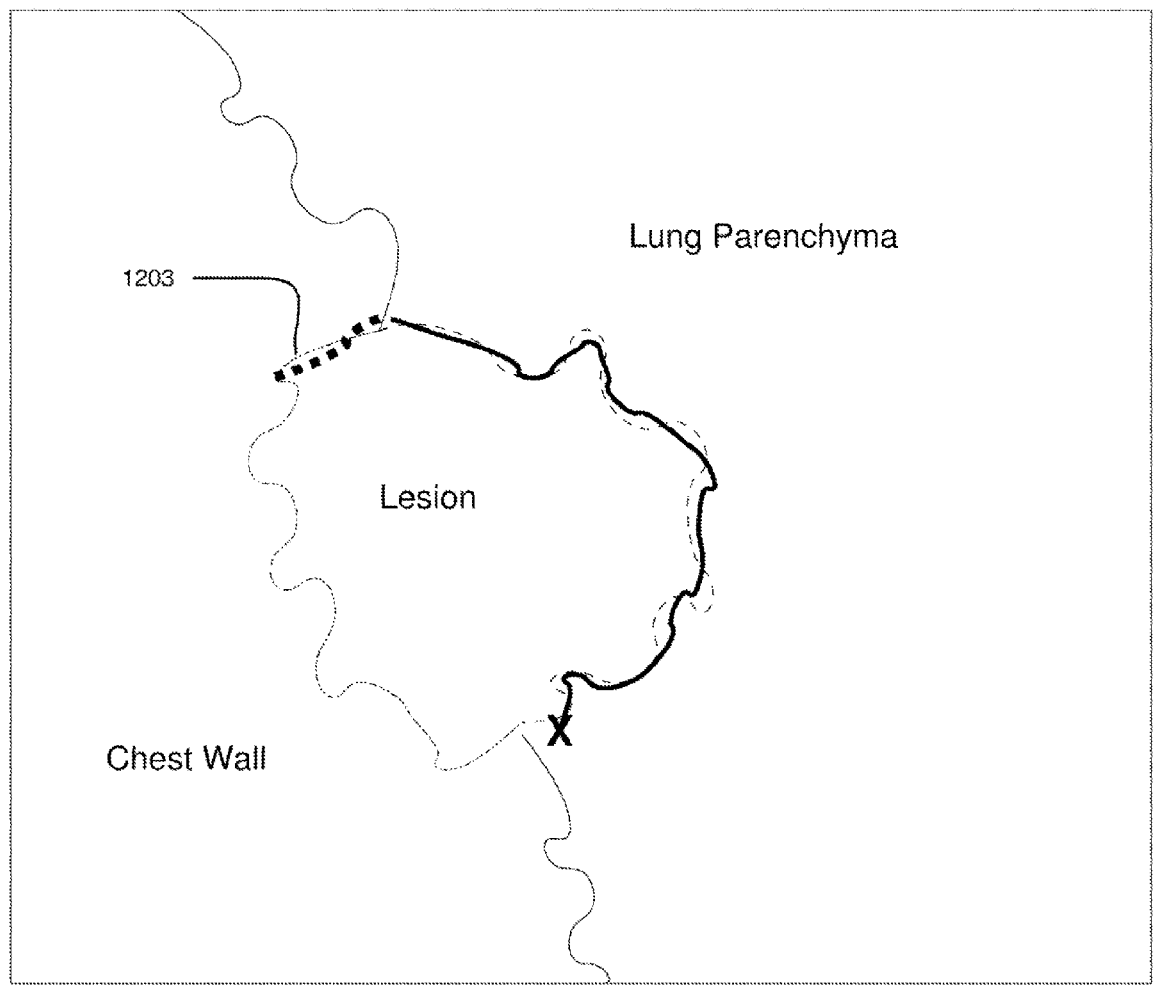
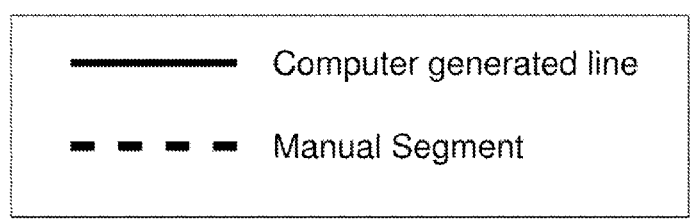
Figure 12 D, user starts boundary in difficult region

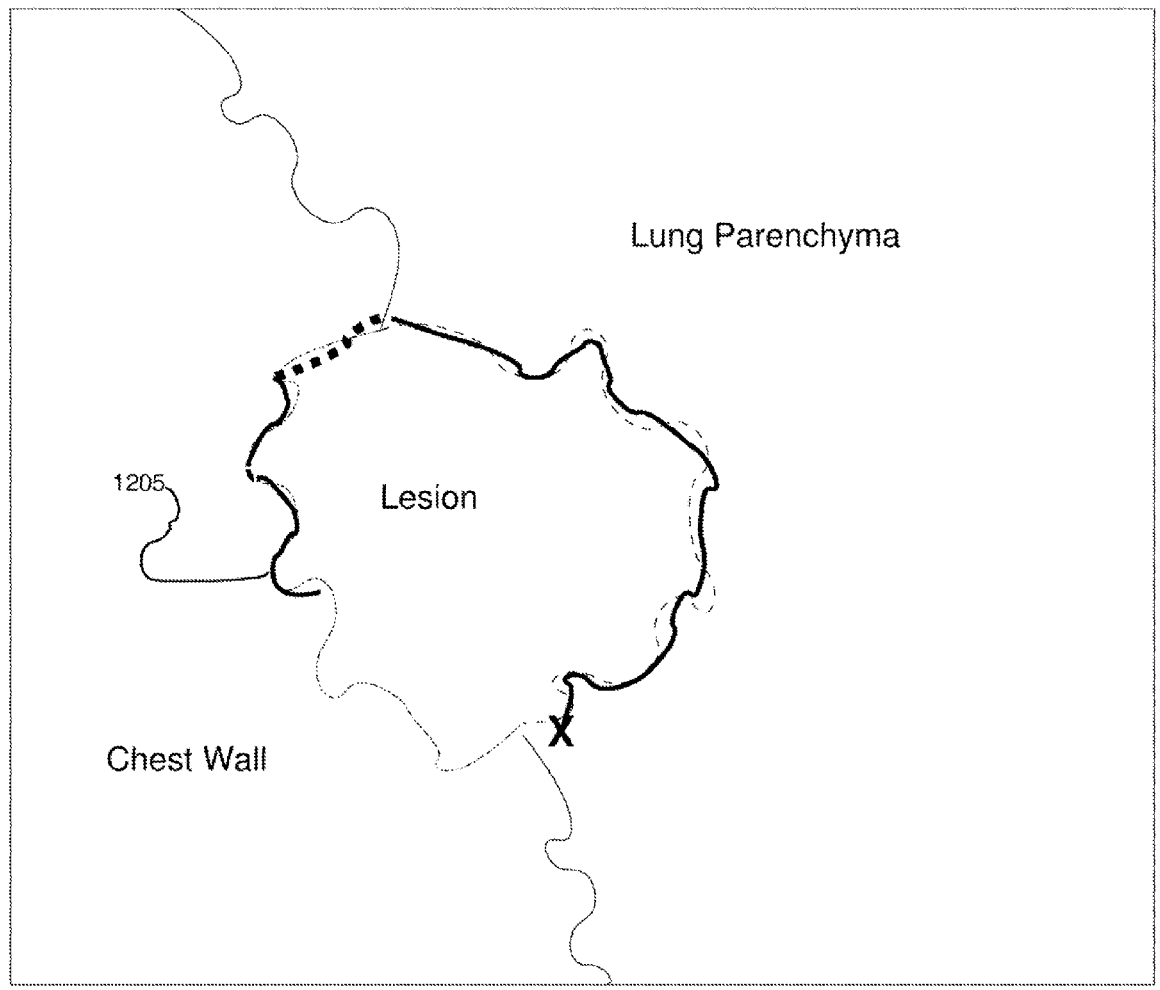
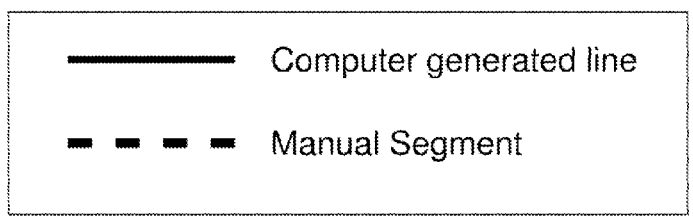
Figure 12 E, computer extends boundary as far as possible

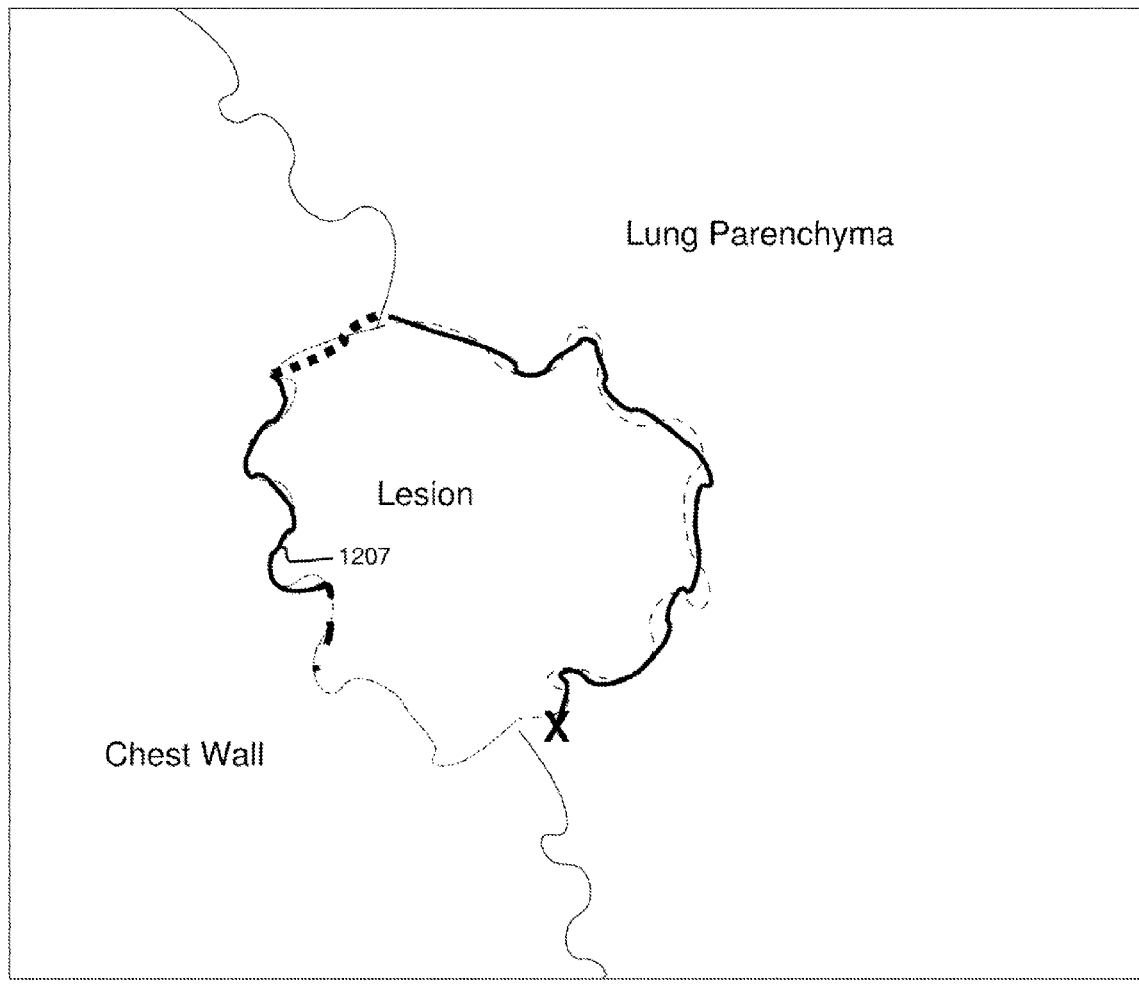
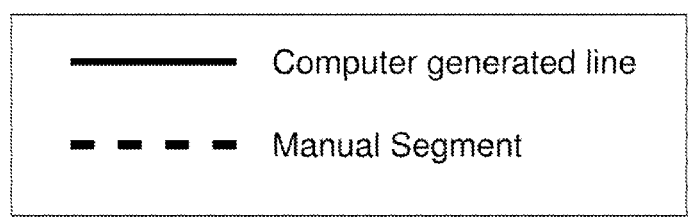
Figure 12 F, user provides second marking

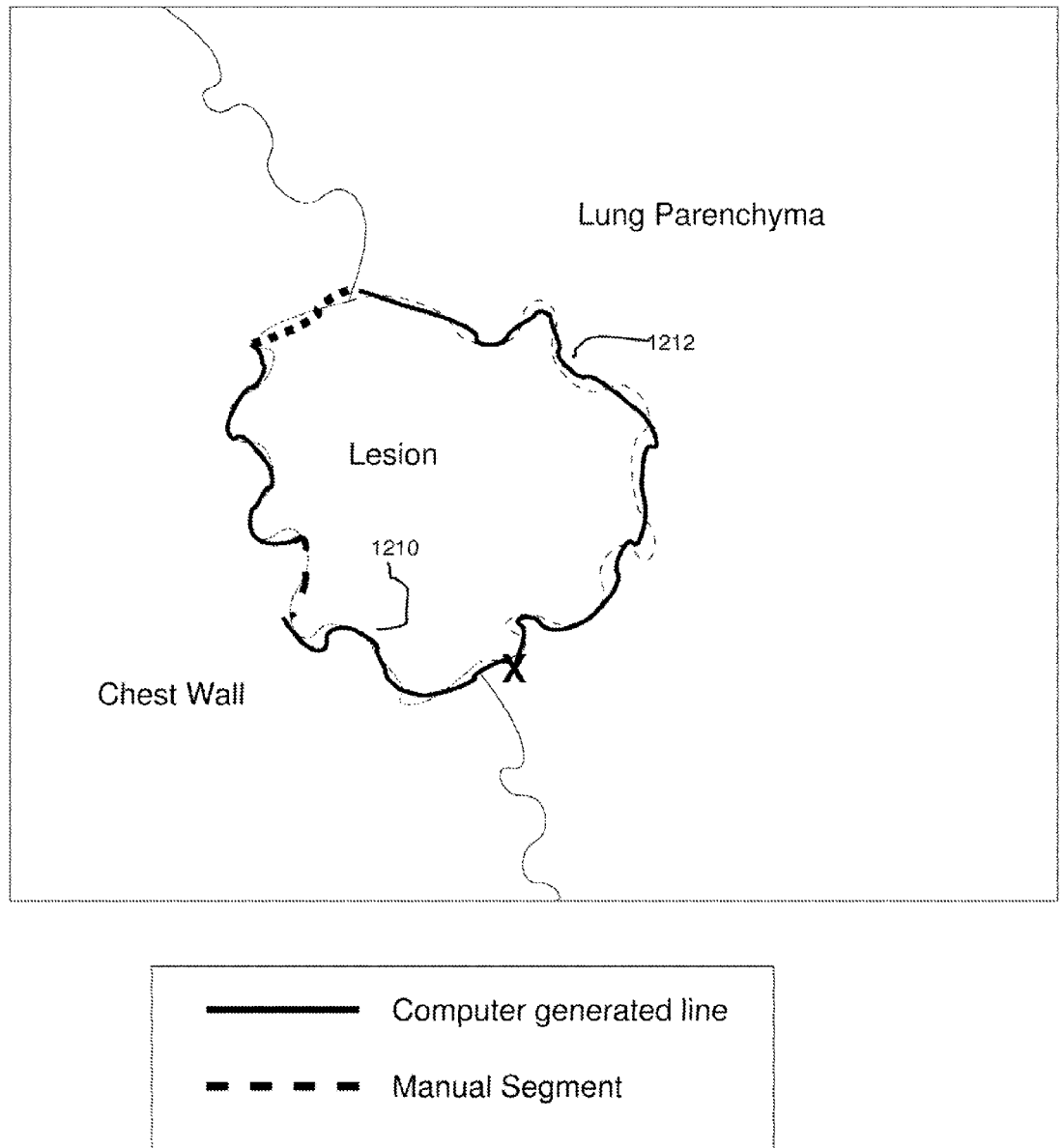
Figure 12 G, Computer compleates boundary

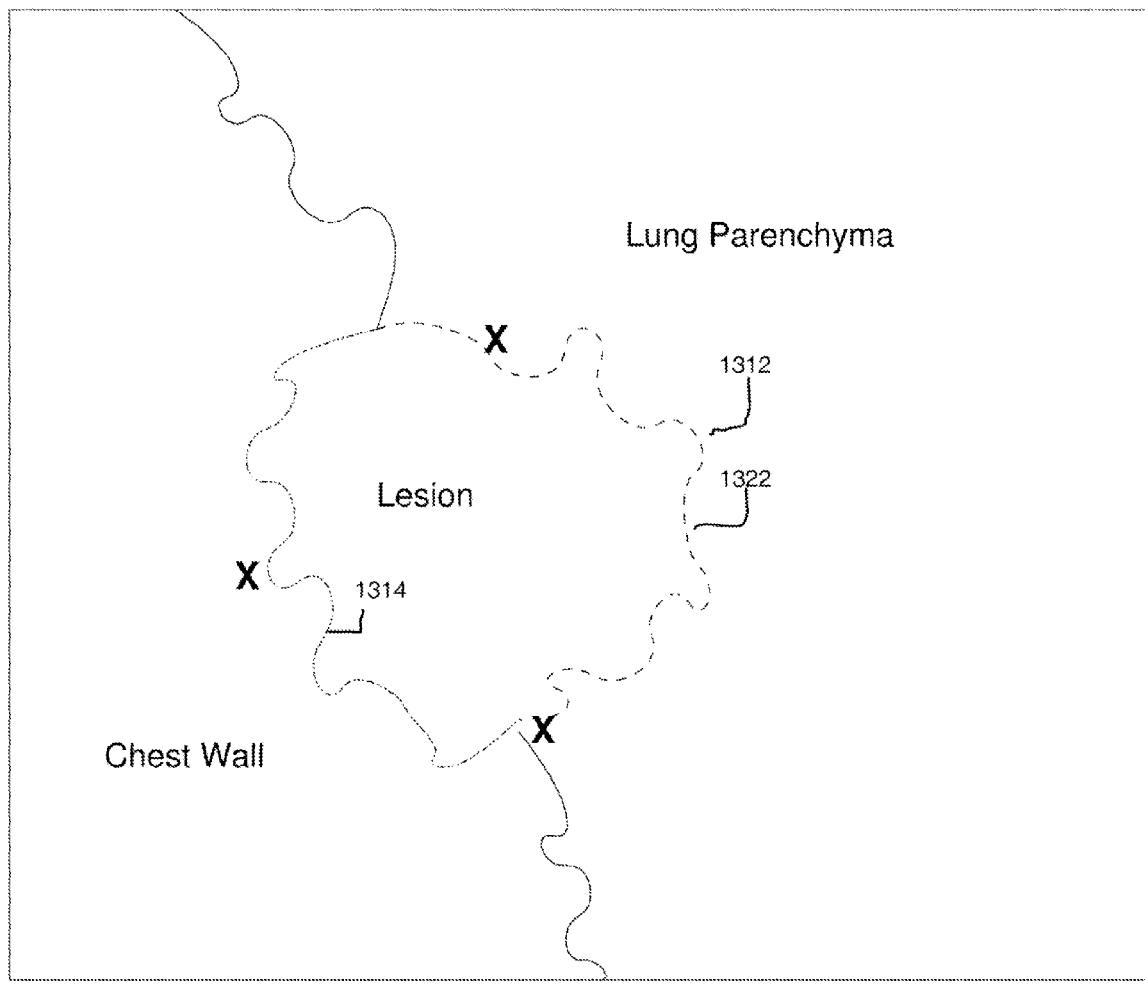
Figure 13 A, Original Image with 3 user specified marks

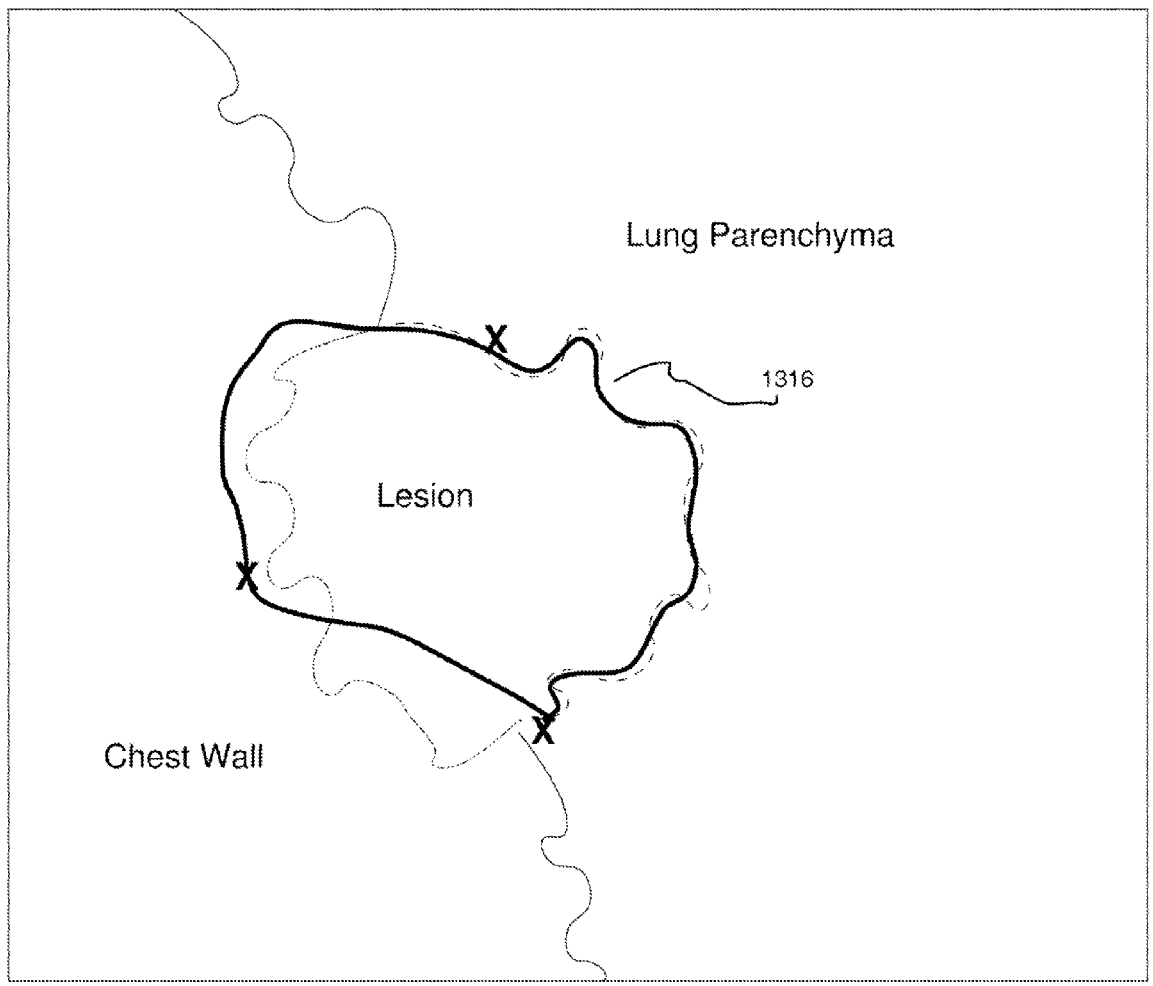
Figure 13 B, First Computer Generated Boundary

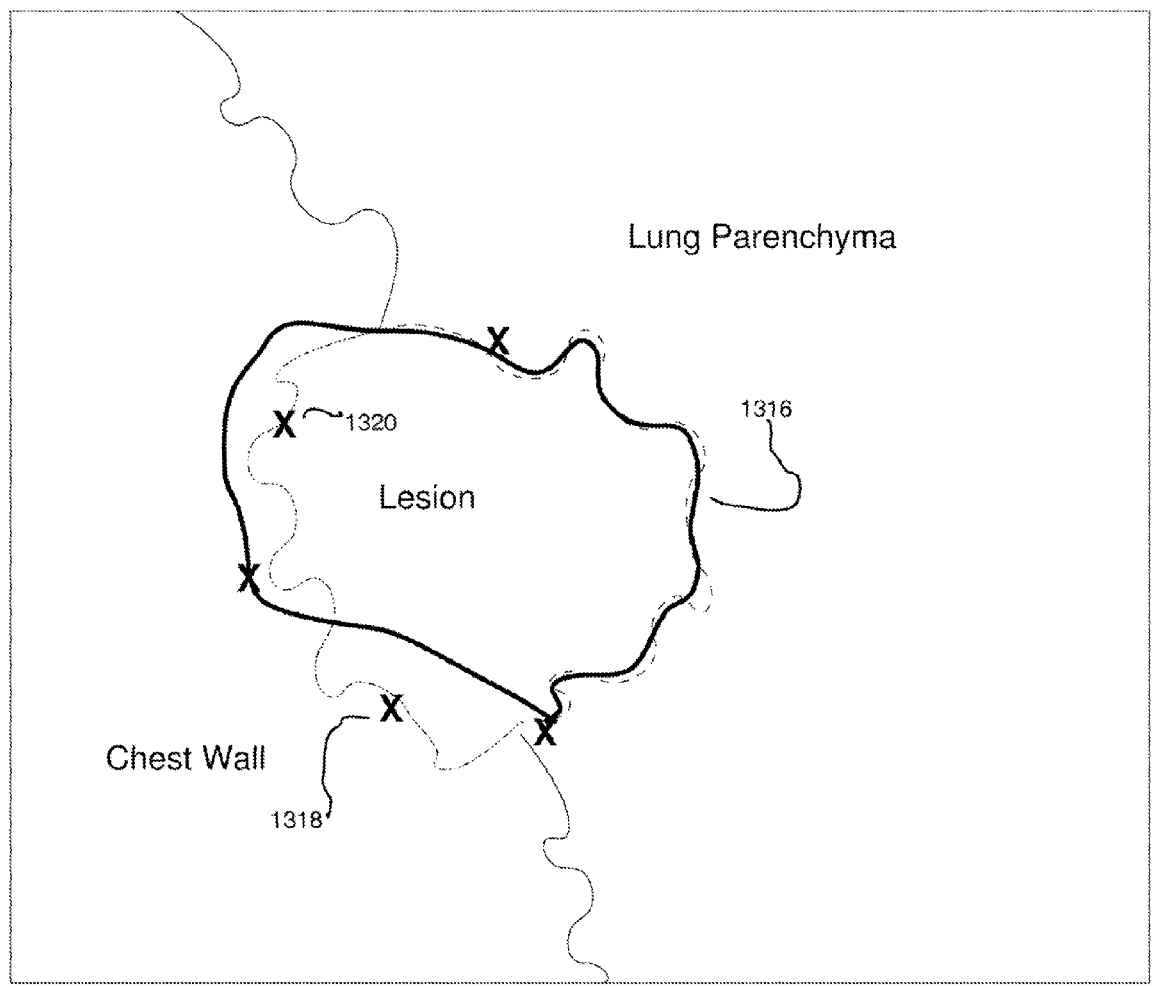
Figure 13 C, User adds two additional points

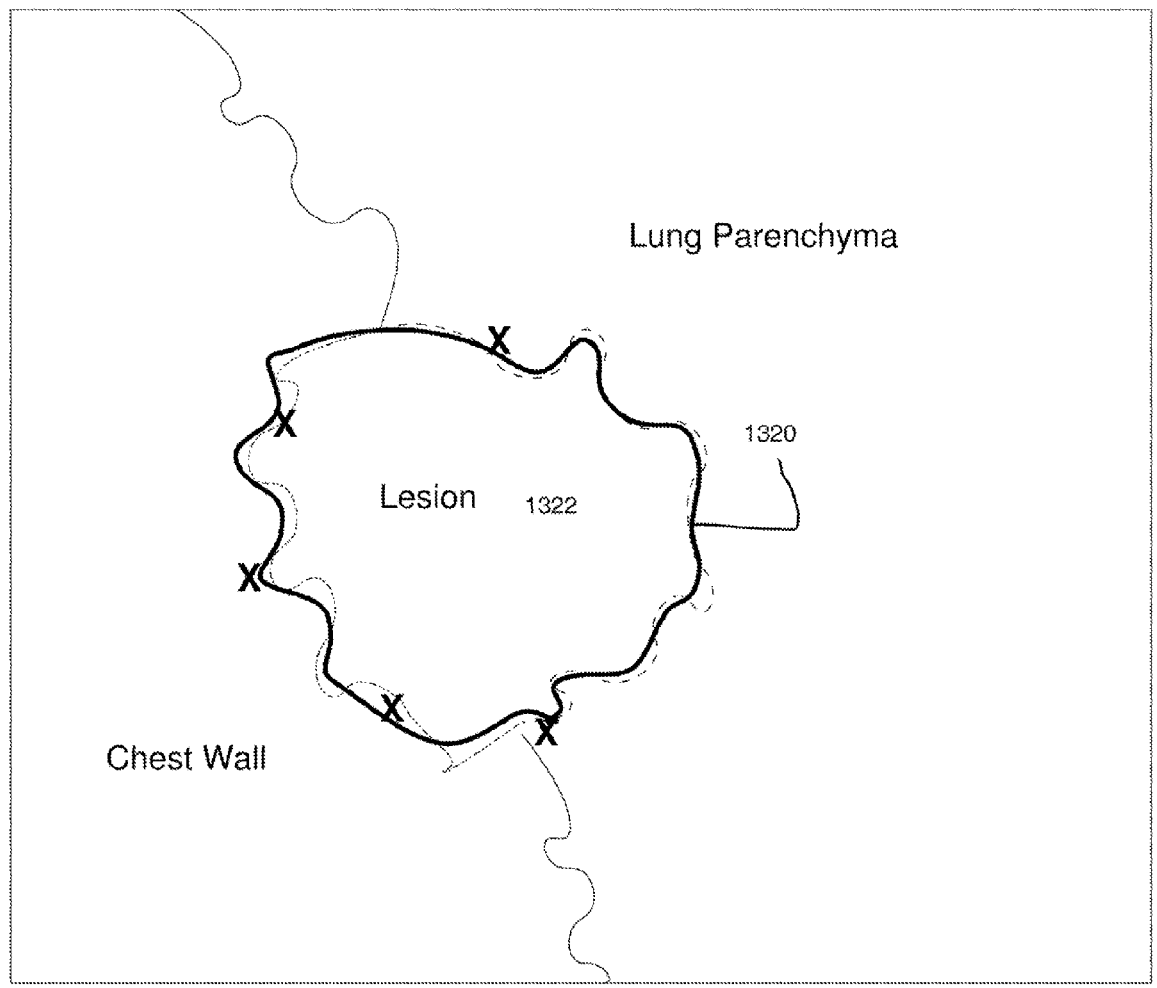
Figure 13 D, Final Computer Boundary

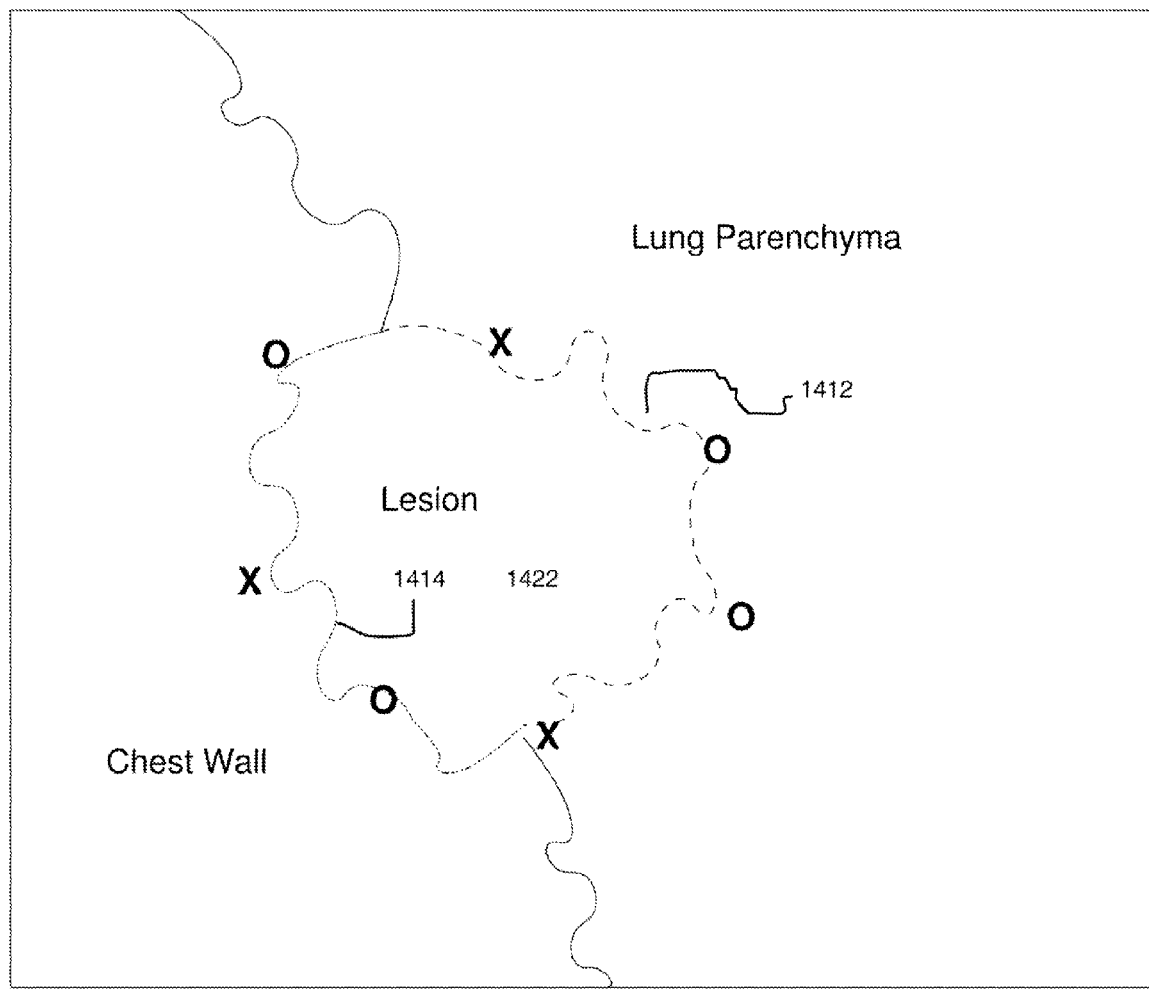
Figure 14 A, Adjacent image with boundary marks

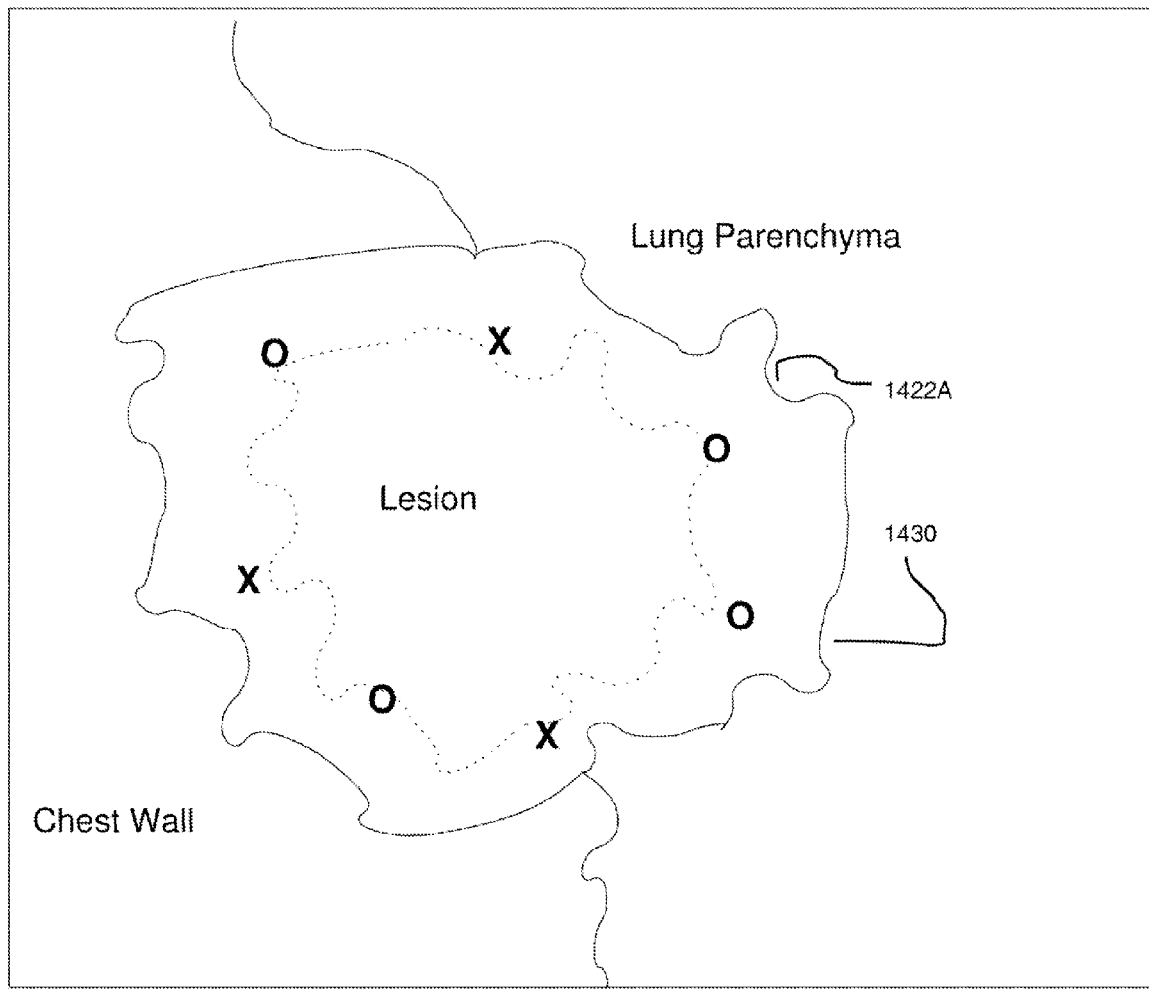
Figure 14 B, Boundary ponts copied to current image

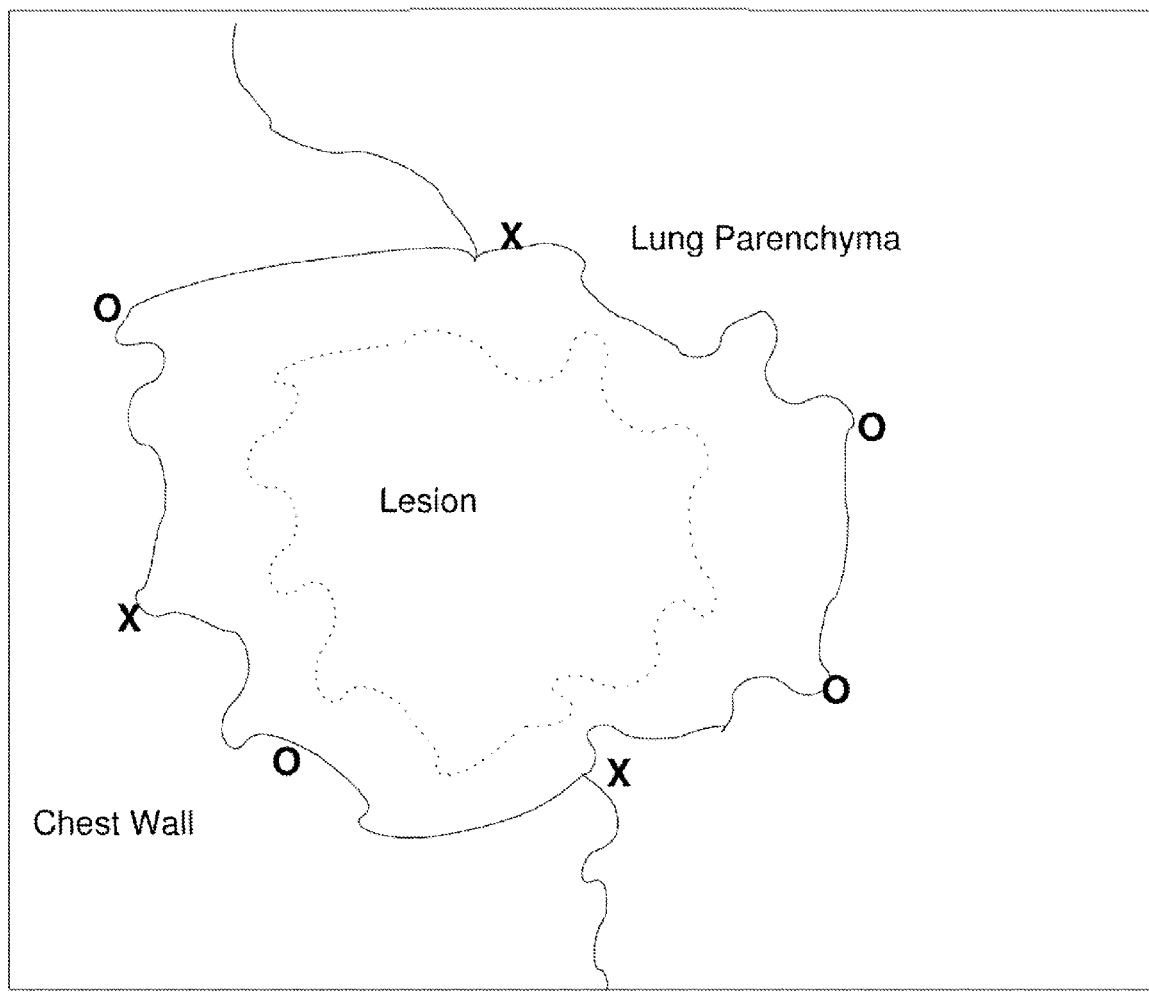
Figure 14 C, Boundary points moved to new boundary

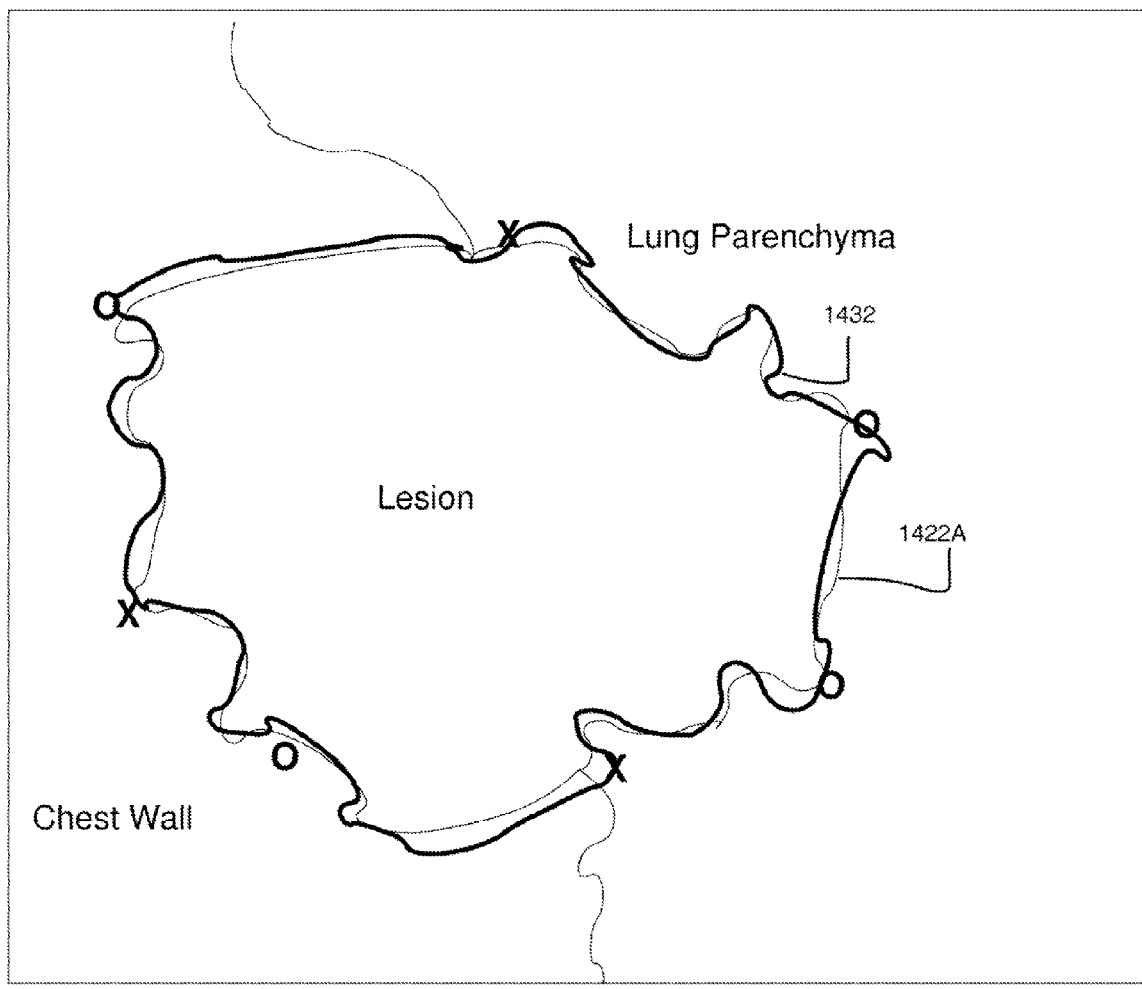
Figure 14 D, Computer generated boundary through boundary points

MEDICAL IMAGING SYSTEM FOR ACCURATE MEASUREMENT EVALUATION OF CHANGES IN A TARGET LESION

RELATED APPLICATIONS

This application claims priority from co-pending international application number PCT/US2005/013968, entitled MEDICAL IMAGING SYSTEM FOR ACCURATE MEASUREMENT EVALUATION OF CHANGES IN A TARGET LESION, having international filing date Apr. 25, 2005, which, in turn claims priority from U.S. Provisional application Ser. No. 60/565,327, of the same title, filed Apr. 26, 2004, both applications are incorporated by reference.

FIELD OF THE INVENTION

The present invention relates generally to analysis of medical imaging data, and, more particularly to an automated computer process for accurate measurement evaluation of changes in a target lesion or multiple target lesion as imaged by a medical imaging system.

BACKGROUND OF THE INVENTION

The pharmaceutical industry develops a variety of products that require approval from the FDA often based on measurements derived from medical images. One of the most expensive and time-consuming aspects of drug development relates to clinical trials for getting anticancer agents such as anticancer drugs approved. This is particularly evident in the field of oncology, although it is also applicable to other medical fields.

In the field of oncology, the use of medical images for assessing response to an anticancer agent treatment is now commonplace. Many clinical trials use measurements of variations in the size of an abnormality or lesion, such as a tumor, as the prime indicator of treatment effect. Although change in patient survival is considered a primary endpoint, along with others, in making the evaluation of drug effectiveness, this metric, by necessity, is evaluated less frequently than the surrogate endpoint of change in tumor size as a means of receiving FDA approval. For example, a drug used to treat lung cancer might be evaluated using criteria based on the rate of reduction in size of a tumor or other lesion in the lung.

RECIST (Reponse Evaluation Criteria In Solid Tumors) criterion is a formal method that has been established to measure change in tumor size. RECIST comprises a set of published rules that define when cancer patients improve ("respond"), stay the same ("stable"), or worsen ("progression") during treatments. The criteria were published by an international collaboration including the European Organization for Research and Treatment of Cancer (EORTC), National Cancer Institute, (NCI) of United States, and the National Cancer Institute of Canada Clinical Trials Group. (See Therasse, et al., "New Guidelines to Evaluate the Response to Treatment in Solid Tumors," *Journal of the National Cancer Institute*, Vol. 92, No. 3, Feb. 2, 2000, 205-26). Today, the majority of clinical trials evaluating cancer treatments for objective response in solid tumors are using RECIST.

The essence of the RECIST criterion is the use of a single dimensional measurement wherein an image containing the largest cross-sectional diameter of the tumor is selected and the largest measurement in one dimension is obtained from that image. The one dimensional measurement is then compared at a specific time to a comparable image of the same tumor to assess for response. According to RECIST, complete response is defined as disappearance of the tumor, partial response is defined as a 30% decrease in size, and progression is defined as greater than a 20% increase in tumor size. RECIST does not consider lesions smaller than 1 cm.

In taking any measurement, accuracy is a critical issue. Unfortunately, the current RECIST approach for assessment of tumor response to treatment is severely limited because it does not consider measurement accuracy. As a result, it suffers from the need to observe large changes in single dimensional measurements in order to determine if there has been a response to treatment. The need for such large changes relates to an inability to reliably make measurements of a tumor size.

In previous standard practice, caliper measurements made by radiologists have been used to measure tumor size. The accuracy of measurements has been estimated by measuring variability of expert radiologists in measuring either phantom or actual nodules. Errors related to manually measuring tumor lengths can be quite large. Similarly, the inability to reliably select comparable imaging planes on temporally separated scans necessitates reliance on large changes in order to be certain that the change is genuine and not one of measurement error.

Other systems, such as presented in Kaufman et al., U.S. Pub. No. US 2003/0016850 A1, published Jan. 23, 2003 only compare two superimposed images. However, methods for accurate measurement evaluation including, among others, determining a bound on the error of a size change measurement are lacking.

Generally, current methods do not offer a process for accurate measurement evaluation having steps in accordance with the present invention that use volumetric methods for size determination. Current methods measure the extent of the tumor in one slice and in only one or two directions, rather than measuring all voxels associated with the tumor.

SUMMARY OF THE INVENTION

The present invention provides an automated method for determining a bound on the error of a volume change measurement. A body part is scanned to produce a first set of imaging data. A target lesion in the imaging data is identified. The body part is rescanned at a subsequent time so as to produce a second set of imaging data. The target lesion is identified in the second set of imaging data and the size of the target lesion is measured in the first and second sets of imaging data to determine two apparent image volumes corresponding to the first and second sets of imaging data. A change in size is estimate by comparing the first and second apparent lesion sizes. A variance on the change in size is estimated so as to determine a bound on the change in size measurement.

In one aspect, the present invention offers a method for shortening the length of clinical trials by providing an accurate method for learning whether a tumor is responding or not in shorter time intervals.

In another aspect, the present invention offers a method for confidently measuring smaller degrees of change in a tumor to provide information useful for therapeutic response.

In another aspect, the present invention offers a method for confidently measuring smaller degrees of change in a tumor to provide information useful for diagnostic response.

In another aspect, the present invention offers a method for confidently measuring smaller degrees of change in a tumor to provide information useful for diagnostic applications.

BRIEF DESCRIPTION OF THE DRAWINGS

While the novel features of the invention are set forth with particularity in the appended claims, the invention, both as to organization and content, will be better understood anti appreciated, along with other objects and features thereof, from the following detailed description taken in conjunction with the drawings, in which:

FIG. 8A and FIG. 8B schematically show another alternative embodiment of a nodule boundary visualization method superimposed on CT images acquired at different times;

FIG. 10 schematically shows another alternate embodiment of a nodule boundary visualization method superimposed on a CT image; and FIG. 11 schematically shows yet another alternate embodiment of a nodule boundary visualization method superimposed on a CT image.

FIG. 12A-FIG. 12G illustrate an example of the use of drawing tools as employed by an imaging system constructed in accordance with one embodiment of the present invention.

FIG. 13A-FIG. 13D illustrate another example of the use of drawing tools as employed by an imaging system constructed in accordance with one embodiment of the present invention.

FIG. 14A-FIG. 14D illustrate yet another example of the use of drawing tools as employed by an imaging system constructed in accordance with one embodiment of the present invention.

DESCRIPTION OF THE PREFERRED EMBODIMENTS

Preliminarily, it should be noted that, while a particular system and method is described in detail herein for analyzing medical imaging data, such as radiology data, this is not by way of limitation, but solely for the purposes of illustration, and the invention may also be employed for analyzing data of other types.

The present invention builds on advances in imaging technology that have now made it possible to scan tumors such that the entire tumor volume is imaged. There have been significant improvements in the methods for the measurement of tumor size from CT images over the last decade by using 3D volumetric computer algorithms. In addition, images are not obtained isotropically, meaning that the resolution is nearly the same in the x, y, and z dimensions. Advanced image processing allows for improved segmentation of the tumor from surrounding structures, with better definition of the tumor boundaries, thus leading to improved measurements.

The present invention uses a combination of higher resolution imaging techniques and advanced image processing to compare tumors more accurately. In this way, smaller degrees of change can be measured while maintaining confidence in measuring tumor size changes. In addition, changes can be measured volumetrically rather than using a simple one-dimensional measurement. In this way, a more complete assessment of the data can be made.

Measurement accuracy depends upon a large number of factors. By estimating the error associated with each of these factors an accuracy for any specific tumor measurement can be determined. As a result of knowing the measurement accuracy, a much tighter bound can be provided on the size change of a tumor to indicate a significant event. Thus, by using an accuracy analysis, a significant event can be identified earlier and more reliably while using a smaller, but more accurate, size change in a tumor, than by using the existing RECIST criterion.

An existing clinical trials data management system called the ELCAP Management System (EMS) may advantageously be used in connection with the method of the invention. EMS provides for all aspects of trial management system including remote radiologist reading and computer analysis of image data. The innovative capabilities of EMS allow for more efficient and timely management of clinical trails, resulting in a shorter time to conduct a trial while using more accurate data measurements and superior quality control. The amount of data loss characteristic of clinical trails due to poor patient protocol monitoring at participating sites is also improved by the use of a web-based system with real-time feedback and reporting. In addition to automated methods, a semi-automated method that allows the radiologist to manually draw certain delineating boundaries to set limits for the area or volume measurements will improve overall reproducibility and accuracy.

Figure 1:
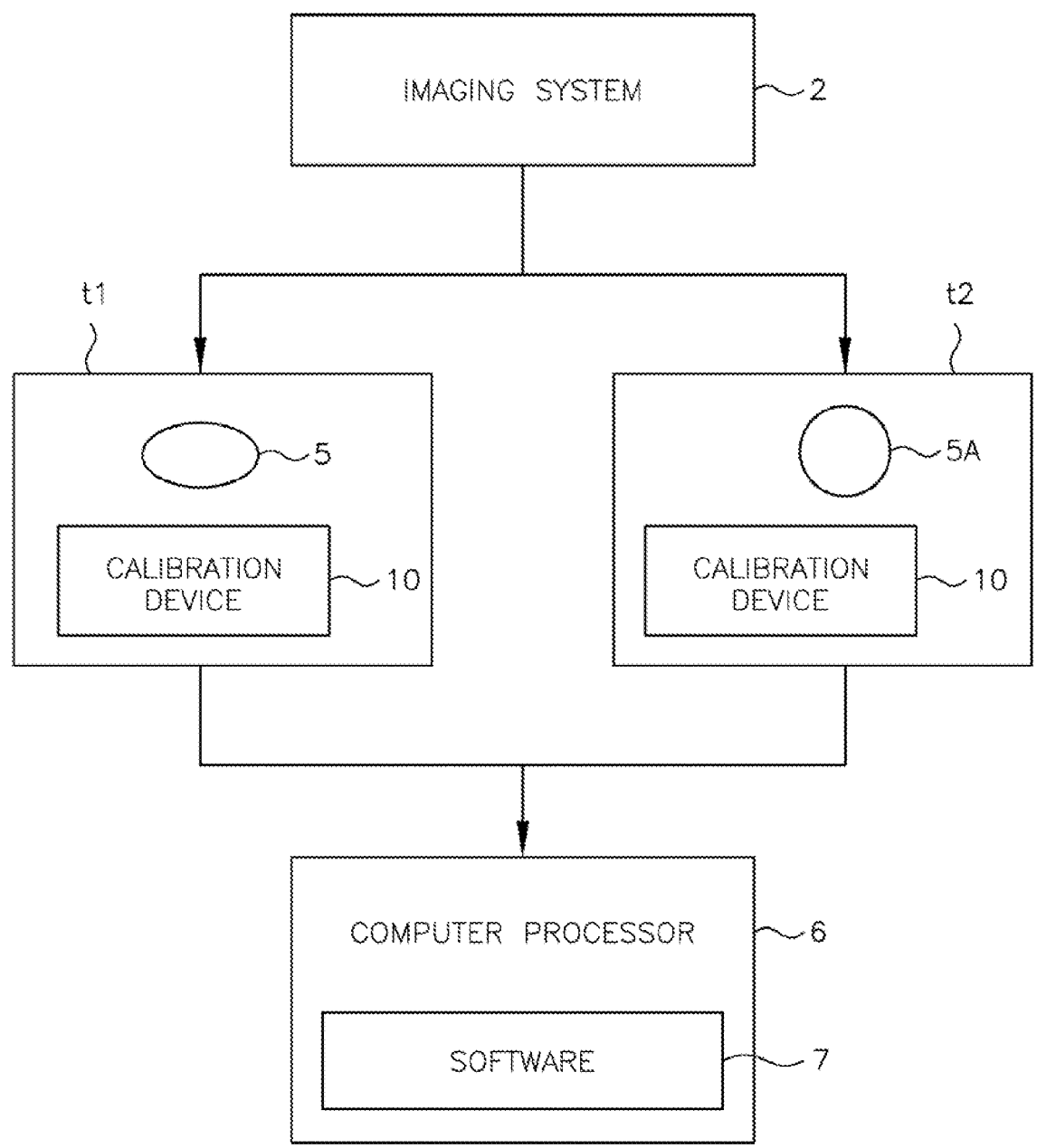
FIG. 1 shows a simplified block diagram of a system for accurate measurement evaluation of changes in a target lesion as imaged by an imaging system constructed in accordance with one embodiment of the present invention.

Referring now to FIG. 1, there shown is a simplified block diagram of an automated system for accurate measurement evaluation of changes in a target lesion as imaged by an imaging system as constructed in accordance with one embodiment of the present invention. An imaging system 2 produces image data at differing times $t_1$ and $t_2$. A target lesion 5 in the image data at time $t_1$ also appears in the image data at subsequent time $t_2$ as target lesion 5A. That is lesion 5 is the same lesion as lesion 5A, but differences in the volume sizes of the target lesion at different times are here presumed due to anticancer agent treatment for exemplary purposes. The image data is processed in computer processor 6 running image processing software 7. Target lesions may include cancerous tumors, nodules and the like. The images may also include a calibration device 10, discussed further in detail below.

The medical imaging system 2 may advantageously include any known medical imaging system. Some useful known imaging systems include computerized tomography scanners, magnetic resonance imagers, positron emission imaging systems, X-ray imaging systems vascular interventional and angiogram/angiography procedures, ultrasound imaging systems and equivalent medical imaging systems. Scanned target lesions 5 may advantageously include tumor types specified for application of World Health Organization (WHO) and RECIST criteria including breast, lung, melanoma, colon, ovary, and sarcoma tumors.

In one useful embodiment of the invention, the software 7 automatically, operates to accurately measure size and volume of the target lesion 5. In this way a change in volume can then be estimated given a time difference between acquiring image data of the target lesion 5. The method of the present invention determines the degree of error associated with each measurement in order to estimate the volume and ultimately the proportional and/or actual change in the volume. Automatic methods implemented under computer control provide precise repeatability. Calibration methods estimate the measurement error due to scanner artifacts. Modeling, simulation and actual nodules function to characterize the measurement accuracy with respect to different nodules and their corresponding appearances in images, such as CT images.

Numerous features of lesions are assessed to determine the variance in the measurement of a given volume based on its apparent volume. Measurements will vary depending on the differences in the signal of the lesion versus background. Measurement error variance may advantageously include an estimates reflecting various portions of a lesions, such as a nodule that may have a particular edge characteristic.

Thus, for a given definition of boundary for a particular edge, an estimate can be made regarding the variance of the measurement. As discussed below, other factors that may advantageously be estimated include the extent to which adjacent structures are attached to a target lesion, and the influence adjacent structures may have on volume estimates. Characteristics of the measuring device may also be included as factors influencing error variances. Volume measurements may also be affected be affected by the inherent resolution of the imaging system itself as well as by the amount of noise present in the image.

Spatial Calibration

Standard calibration methods include the scanning of phantoms and measuring the quantities of noise, scanner artifacts and image distortion. Phantoms are synthetic objects having known dimensions. Due to the physical properties of an imaging system, such as, for example, a CTS scanner, these factors are spatially dependent. That is, the measurement error varies according to the location of the measurement within the body and the position of the body within the scanner. Current practice does not take advantage of such factors, but instead uses a conservative global distortion figure as provided by the manufacture.

By conducting phantom studies, maps that characterize the degree of image distortion, image artifacts and noise for all pertinent regions of the human body may advantageously be established for a given imaging system. Once established, the maps can be used to determine a more accurate bound for the measurement error of the measurement of a tumor.

Error Correction

Accurate computer measurement of tumor size from CT images employs an algorithm for determining the exact location of junctions between a lesion and other tissue. The algorithm may process many different types of lesions and use different strategies to resolve different situations. An error estimate may be made based on the form of the image and the details of the specific algorithmic process for that image. In one aspect of the invention a database is created for each identifiable image distortion and a measurement error estimate is made from the statistical variation within the database.

In accordance with the present invention, approaches for system error estimation include (a) measurements from CT images of calibrated phantoms, and (b) measurements from multiple scans of actual lesions from patients. In one useful embodiment, measurements from slow growing lesions may advantageously be obtained with short intervals between scans.

An another example, repeated images of lesions may be scanned at very short intervals regardless of growth rate to provide error estimates based on a substantially unchanged lesion. Such repeated images may be obtained during a biopsy wherein multiple images of a lesion are obtained within a few seconds. In addition, when a human observer is involved in the measurement process the variation or error due to the human interaction can be obtained by human observer trials involving either phantoms or repeatedly scanned lesions.

Error associated with specific geometric situations (e.g. a nodule attached to the chest wall) can be estimated by taking multiple images of a set of phantoms that mimic the situation. The variation between the scans of a synthetic phantom can be used to characterize the error boundary for each specific situation tested.

By taking multiple measurements of phantom images, good characterization of the scanner system variation parameters can be obtained. For example, scanner reconstruction properties such as the point spread function can be accurately determined by the analysis of phantom studies and experiments. However, phantom data cannot initiate all situations because come nodules exhibit subtle changes in density that are difficult to model. In such cases multiple scans of a number of such nodules that do not exhibit apparent growth can be used to create a nodule database. One way to do this is by comparing two scans of the same lesion taken within a short time interval. The nodule database can then be applied to measure the measurement variation between scans in order to estimate the measurement error for a given class of difficult nodules.

Specific imaging problems may give rise to specific image artifacts. For example, heart motion produces a ripple in the z-dimension of the three-dimensional image shape. As a further example, bones in the apical region can produce excessive amounts of noise. These and other particular conditions can be identified and error bounds may be estimated from a database of similar cases.

Error Estimates When Manual Intervention is Required

In some difficult imaging situations a radiologist may intervene in the nodule segmentation process. Further processing by computer algorithms may then reconcile the differences between the radiologist's decisions between scans. As estimate of the measurement variation due specifically to the radiologist's intervention by establishing a database of such cases. Once all sources of measurement error have been determined an overall measurement error can be computed.

Figure 2:
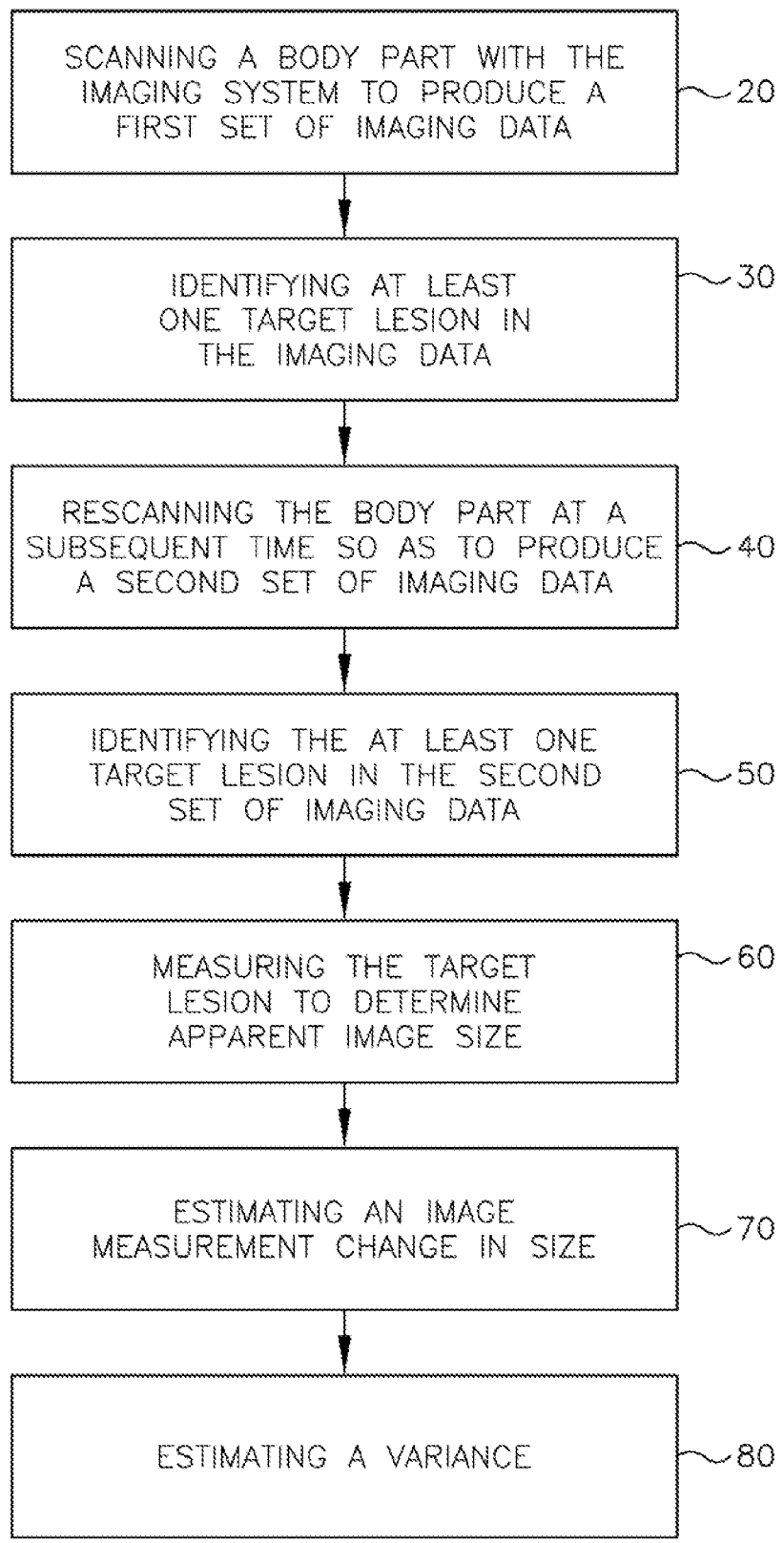
FIG. 2 is a high-level functional block diagram of an automated method for determining a bound on the error of an image measurement constructed in accordance with one embodiment of the present invention.

Referring now to FIG. 2, there shown is a high level functional block diagram of an automated method for determining a bound on the error of a size change measurement, in accordance with one embodiment of the present invention. The automated method for determining a bound on the error of a volume change measurement comprises the steps of:

scanning a body part with an imaging system to produce a first set of imaging data at step 20;

identifying at least one target lesion in the imaging data at step 30;

rescanning the body part so as to produce a second set of imaging data at step 40;

identifying the at least one target lesion in the second set of imaging data at step 50;

measuring the at least one target lesion as imaged in both the first set of imaging data and the second set of imaging data to determine a first apparent target lesion size corresponding to the first set of imaging data and a second apparent target lesion size corresponding to the second set of imaging data at step 60;

estimating a change in size by comparing the first and second apparent lesion sizes at step 70; and estimating a variance on the change in size so as to determine a bound on the change in size measurement at step 80.

The step of estimating a variance on the change in size at step 80 may advantageously include results from assessing a plurality of factors that affect measurement accuracy. Standard statistical methods may be employed to estimate or otherwise determine the image measurement variance and other error measurements discussed herein. Such techniques include, for example, linear regression, random effects models and the like.

Factors that affect measurement accuracy include primary sources of error like nodule form, scanner parameters, patient factors, algorithm and operator factors. Many of these are interrelated. For example, the definition of the boundary of the nodule will depend upon the nodule tissue, the point spread function of the scanner, patient motion, and other factors. Estimate of error variation are obtained using image models for the error factors and obtaining the parameters for these models from measurements on image phantoms and patients and also by computer simulations. Paired observations of the same patient may be used to reduce error.

Example of nodule form factors include:
a. Density distribution characteristics, such as
  i. homogeneous or variable distribution characteristics, and/or
  ii. solid tissue or diffuse tissue characteristics.
b. Geometric shape characteristics of the nodule such as
  i. spherical or complex shapes, where complexity may be estimated, for example, as a ratio of surface area to volume normalized to a sphere (=1),
  ii. shapes of multiple components,
  iii. cavities, and/or
  iv. small features close to the reconstruction resolution.
c. Surface characteristics such as whether the nodule is rough (i.e. exhibiting a complex surface) or smooth, where a rough surface implies high average curvature.

Examples of scanner parameters include:
a. Reconstruction resolution further including slice thickness, overlap, and/or in-plane pixel size,
b. X-ray energy (dose): kVp and mAs,
c. Reconstruction filter;
d. Gantry rotation speed,
e. Table speed (pitch),
f. Spatially varying point spread function, and/or
g. Calibration.

Examples of patient factors include the following:
a. Location of the scanned area in the body,
b. Size of the body,
c. Degree of inspiration,
d. Respiration motion (especially at the base of the lungs),
e. Small muscle spasms,
f. Lungs apical region, for example, streaking artifacts, and/or
g. Health of the lung tissue adjacent to the nodule, noting the presence of scars, emphysema, or other health-related conditions.

Operator factors result from operators that assist in the nodule measurement process. For example, an operator may manually modify the estimate nodule boundary resulting in a measurable contribution to the measurement error that can be characterized by observer studies.

Completely automated algorithms typically have situations that are close to intrinsic decision points. Foe example, an automated algorithm may consider a peripheral bump on a lesion to be an attached vessel or a part of the nodule. Algorithms may be instrumented to indicate how close to decision points they operate and hence factor in the error associated with falling on the other side of the decision point.

Once an image region has been determined to represent a nodule the variance of the measurement may be estimated by considering, for example, the following image model factors.

1. Density: Low variance is associated with homogeneous solid tissue density distribution. High variance is associated with high image noise an low or spatially varying density distribution.

2. Shape: Low variance is associated with a spherical shape form and high variation is associated with a highly irregular shape containing many bumps or cavities.

3. Surface characteristics: At the boundary (edge) of the nodule region low variation is associated with a high image gradient and high variation is associated with low image gradient. Further low variation is associated is associated with a smooth surface while high variation is associated an irregular surface with high curvatures. The boundary region between the nodule and other relatively solid structures such as vessels or the chest wall (where there is little or no image gradient evidence of a boundary) must be treated in a different manner. For low variation these boundary regions should be matched between the two scans in the image segmentation algorithm. Since these regions are less accurately determined than gradient edges, the ratio of non-gradient to gradient edge surface areas is directly related to the variation. Assignment of boundaries and incorporation of boundary accuracies using the method of the invention is discussed herein with reference to FIG. 4-FIG. 11 below.

4. Size: In general the larger the nodule, the smaller the proportion of partial voxels the more accurate is the volume estimate. Low variance is associated with large nodules (or very fine scanner resolution) while large variance is usually associated with a smaller nodule (given a similar structural complexity (shape)).

Situations in which the estimated variance may be used include:

A. When two scans are available, all image data and parameters are considered to provide bounds on the estimated growth rate.

B. When a single scan is available, the estimated variance is used to determine the minimum time to wait for taking the second scan in order to obtain a clinically significant decision. That is the time to measure a malignant growth rate within the measurement error bound.

In some situations size will be measured on a two dimensional (2D) area of a single image instead a volume estimated from a set of images.

In a preferred embodiment of the present invention each step is carried out by software that allows for interaction of a medical professional. One useful embodiment of the invention further includes a step of defining the edge of the at least one target lesion in the imaging data. Edge definition may be determined by applying a threshold and/or a gradient function to the ate least one target lesion to determine a boundary for the edge. To further aid diagnosis, the software applies automatic segmentation and classification techniques as are well known in the art to identify boundaries and segment features, including abnormalities, from body parts, such as lungs that are imaged by the imaging system.

In yet another useful embodiment, the method of the invention includes the step of automatically estimating a degree of motion for a particular structure. In yet another useful embodiment, the method of the invention includes the step of automatically estimating a degree of motion for a particular structure includes measuring a degree of variation of surface structures and structures outside of the target lesion. In the lung this will vary markedly with the location of the target lesion relative to the heart.

In yet another useful embodiment, the method of the invention includes the step of automatically matching corresponding images of the at least one target lesion acquired at differing times. For example, the software may select the target lesion having the maximal size in an image and compare it with the comparable target lesion in a second, subsequently acquired image. Size measurements may advantageously include length, area and three-dimensional volume of the lesion.

In yet another useful embodiment, the method of the invention includes the step of selecting the at least one target lesion as an object having a maximal area and finding a comparable object obtained at a subsequent time.

In yet another useful embodiment, the method of the invention includes the step of spatially calibrating an imaging system using at least one phantom and measuring noise, scanner artifacts and image distortion.

Figure 3:
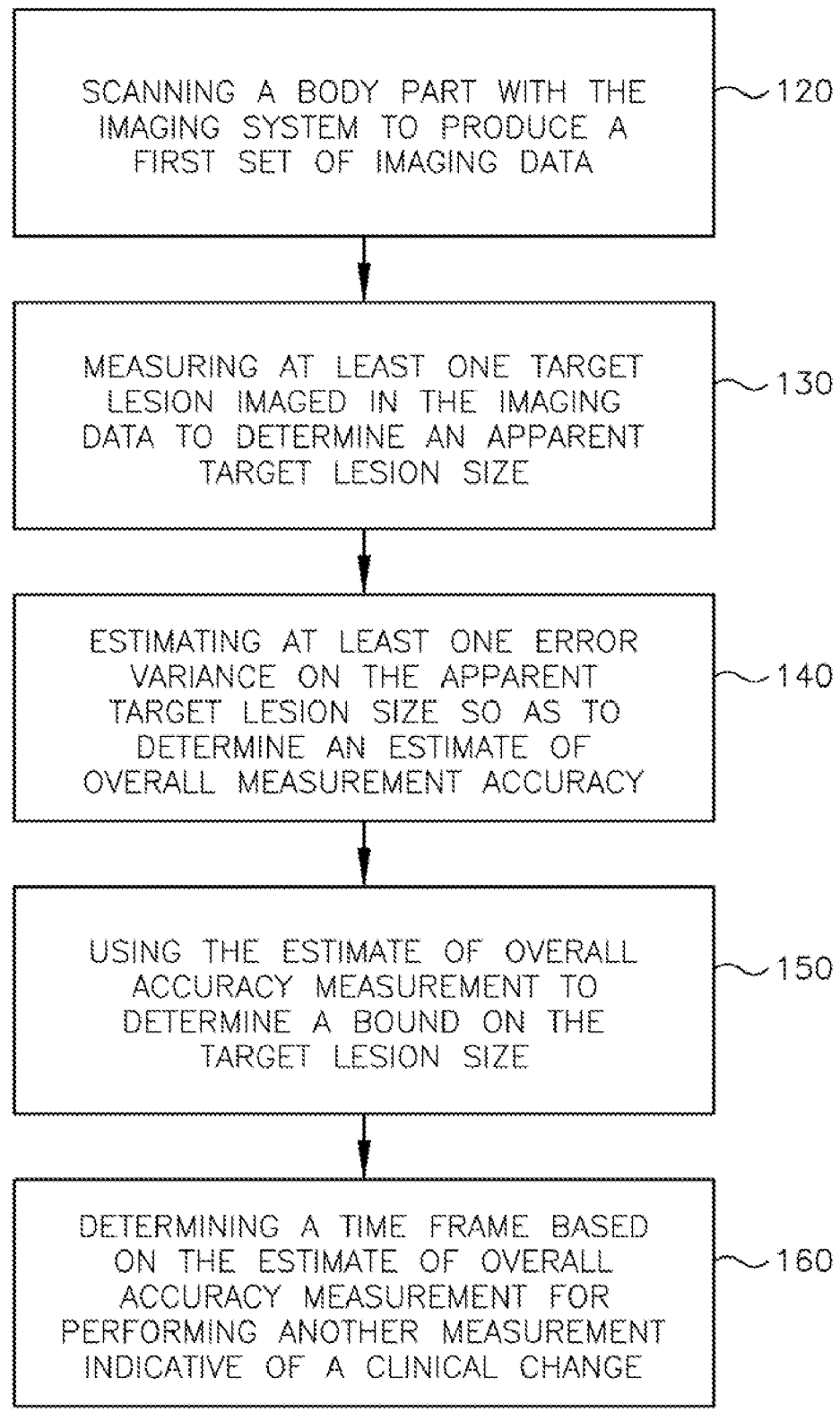
FIG. 3 is a high-level functional block diagram of an alternate embodiment of a method for determining a bound on the error of an image measurement constructed in accordance with an alternate embodiment of the present invention.

Referring now to FIG. 3, there shown is a high-level functional block diagram of a method for determining a bound on the error of an image measurement. Process steps, in accordance with one embodiment of the present invention, include:
   scanning a body part with an imaging system to produce a set of imaging data at step 120;
   measuring at least one target lesion imaged in the set of imaging data to determine an apparent target lesion size corresponding to the set of imaging data at step 130;
   estimating at least one error variance on the first apparent target lesion size so as to determine an estimate of overall measurement accuracy at step 140;
   using the estimate of overall accuracy measurement to determine a bound on the target lesion size at step 150, and
   determining a time frame based on the estimate of overall accuracy measurement for performing a second measurement indicative of a clinical change at step 160.

The method of this aspect of the invention is preferably carried out by software residing on a personal computer. In a preferred embodiment of the invention, the size change of a target lesion to indicate a significant event is smaller than specified by the RECIST criterion. The step of estimating at least one error parameter advantageously includes (a) calculating error measurements from computerized tomography scanner images of calibrated phantoms, and (b) calculating error measurements from multiple scans of patient lesions.

In another useful embodiment of the invention, the software further includes a process module for obtaining a variation due to human interaction using data from human observer trials conducted with phantoms or repeatedly scanned lesions of known size.

In one example embodiment, the set of error factors comprises at least one factor selected from the group consisting of:
   a point spread function of the imaging device and associated reconstruction filters;
   scanner parameters;
   image artifacts caused by high density objects in the same image plane as the nodule;
   patient motion;
   change in patient orientation between scans;
   when scanning the lung, change in body situation or amount of inspiration;
   size of the nodule;
   confounding structures attached to the nodule;
   nodule density variation;
   scanner calibration;
   nodule boundary definition; and
   operator variation, when a human expert interacts with the measurement process.

The scanner point spread function may be estimated by a set of test scans with calibration phantoms. The scanner point spread function may also be estimated by scanning a 3D calibration phantom with the patient. Since the phantom dimensions are known, the scan provides information for estimating any bias due to scanner parameters. The bias information may then be applied to the image data so as to reduce error due to scanner parameters.

Differing scanner parameters between at least two scans may advantageously be measured using a set of phantom scans using both parameter settings to estimate the volume bias due to parameter differences. Ideal practice is to use two scans having the same parameters.

Image artifacts may advantageously be characterized by computing an image noise index based on the spatial frequency content in the region of the object interest, as for example, a nodule or tumor. Image artifacts may also be characterized by data obtained from consistency studies with phantoms having a similar noise index and other parameters provide an estimate of the variation.

Patient motion during scanning may affect results. Common types of patient motion include heart motion, patient muscle spasm, respiration, pulsatile motion or other types of patient motion during the scan of an target lesion, such as a nodule. Patient motion error characterized by heart motion, for example, is detected by repetitive z-axis variation in the imaged nodules surface. In addition to patient motion, patient orientation can affect imaging results. Changes in patient orientation between scans is measured by comparing the orientation of a 3D rigid body matching between at least two scans at differing times.

Changes in patient situation can be measured by a 3D registration between any two scans. Changes in inspiration error may be estimated using studies on a dataset of scan pairs. For large changes in inspiration, studies on a dataset of scan pairs can be used to estimate the bias and variation that this causes.

Where the target lesion is a nodule, nodule size error may usefully be characterized by phantom studies using different sized phantoms to determine the intrinsic measurement variation for a selected nodule size. Similarly, error due to attached structures may be characterized by phantom data using multiple scans and measure variation of the attached structures under different conditions. Attached structures may include, for example, organ abutments or attachments to similar density organs. Error due to attached structures may advantageously characterized by data from nodules of known size where there are attachments and multiple scans compared for segmentation consistency.

Error due to scanner calibration may also be characterized by using histogram matching of image noise from local image statistics. Error due to scanner calibration may also be characterized by using calibration phantoms scanned with the body part.

In one example embodiment, error due to nodule boundary definition may be characterized by comparing a nodule boundary profile with the point-spread function. Error due to nodule boundary definition may also be characterized by conducting phantom studies to determine the variation in volume estimate under different conditions. Error due to nodule density is characterized by comparing multiple scans of slow growing lesions of known size.

In another example embodiment, error due to operator variation may be measured by conducting human observer studies with a number of radiologists and evaluating their variation under different image quality conditions.

As discussed hereinabove, there are several sources of error in making measurements. Selecting certain operational modes when performing a scan, such as keeping the slice thickness constant, can control some error factors. Other factors are intrinsic to the scanning machine such as the Modulation Transfer Function (MTF) of the scanning system. In some cases such intrinsic factors, like MTF, may be specified by the scanning system manufacturer. Currently there is no universally recognized standard for taking images for cancer related measurements. However, the effect of error factors on the measurement accuracy enough to raise the level of confidence about a given measurement using error variance and measurement accuracy measurements can be estimated or otherwise derived as discussed herein. Another way to achieve higher confidence about the accuracy of a measurement is to scan the patient with a calibration device each time.

Referring again to FIG. 1, the present invention optionally includes using a calibration device 10 whenever a patient is scanned where there is consideration of performing volume assessment. The calibration device may comprise a synthetic phantom scanned simultaneously during the patient scan. In this way the synthetic phantom will be subject to the same scanning parameters as the patient. The calibration device can be made available at a scanning center, and/or, in addition, a calibration device can also be given to a patient so that they can the device with them. The calibration device may advantageously contain a set of synthetic phantoms of varying size. The synthetic phantoms may include a set of highly calibrated spherical shaped objects as well as a set of more complex structures.

In one example embodiment, the calibration device set may be held inside an acrylic or plastic casing and be quite small. For example, any easily transportable device ranging in size from about a 2 cm×2 cm×2 cm can up to the size of a standard envelope, typical book or similar items may be used depending on the scale desired. Larger or smaller devices may also be appropriate in some scanning situations. Other calibration devices may include wires, beads, rods and similar items of known size and/or density. The set may be placed on the patient at the time of the scanning and be subject to identical scan parameters. The objects inside the phantom can then be measured. Using multiple objects of different sizes and types, that are highly calibrated for size and density, a measure of variance can be obtained to account for both bias and reproducibility. In this way, the measurement accuracy for a given scanner, using a particular instrument setup when a scan is performed on a given patient, can be estimated. Measurement accuracy may further be enhanced by using additional information known about the scanning device, such as intrinsic factors like MTF as discussed above.

An alternative embodiment of the method of the invention may use an in vivo calibration device or set. For example, wires, beads, catheters, implantable devices or similar items of known dimensions may be in the patient's body for reasons of calibration or other medical reasons. These in vivo devices or elements may be used to calibrate the scan and correlate scanning results and errors at different times, between different scanning situations or both. For example, air within a patient's trachea may be used as an in vivo element for calibration and/or correlation of results.

Figure 4:
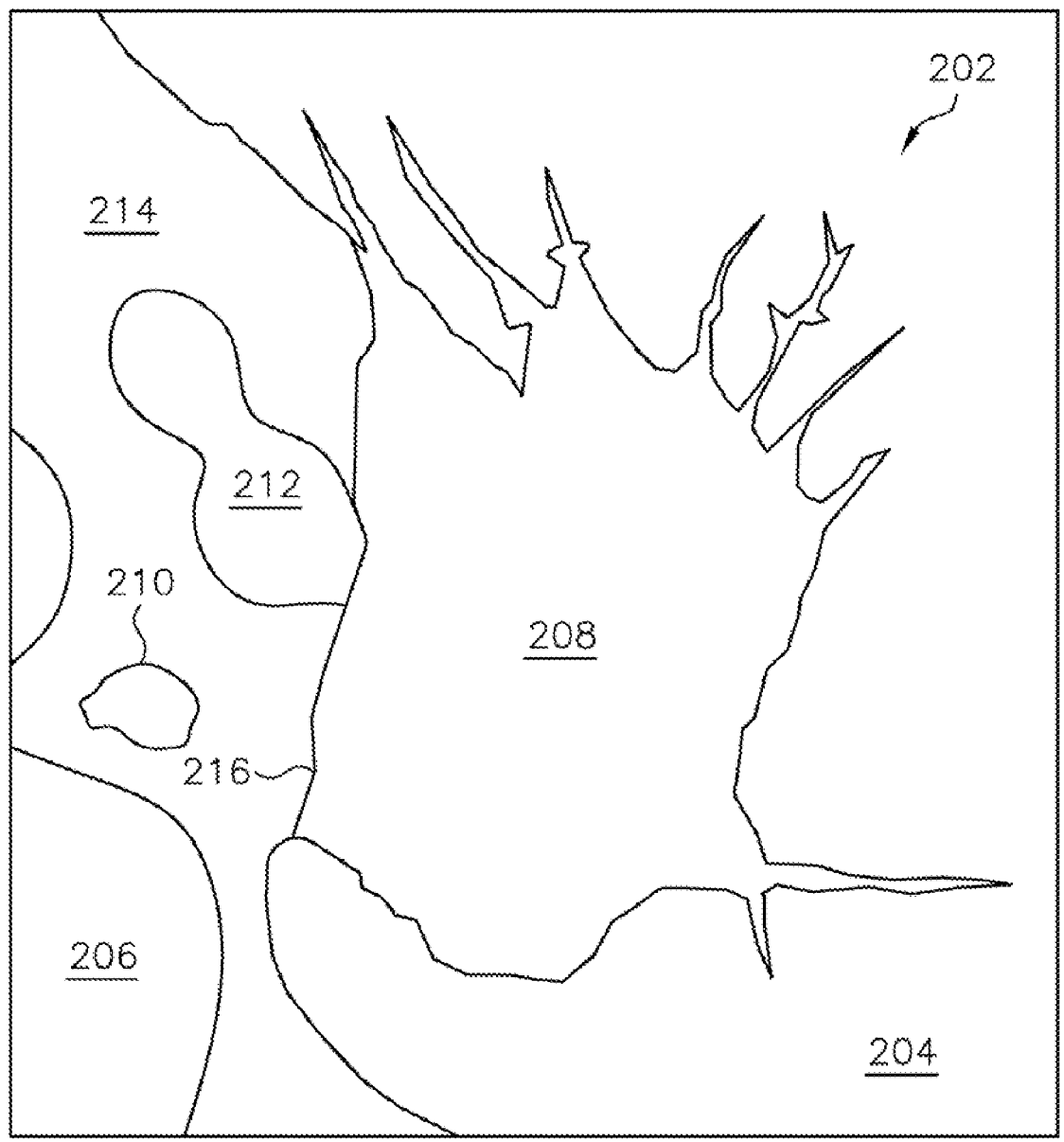
FIG. 4 schematically shows a CT image slice through a large pulmonary.
Figure 6:
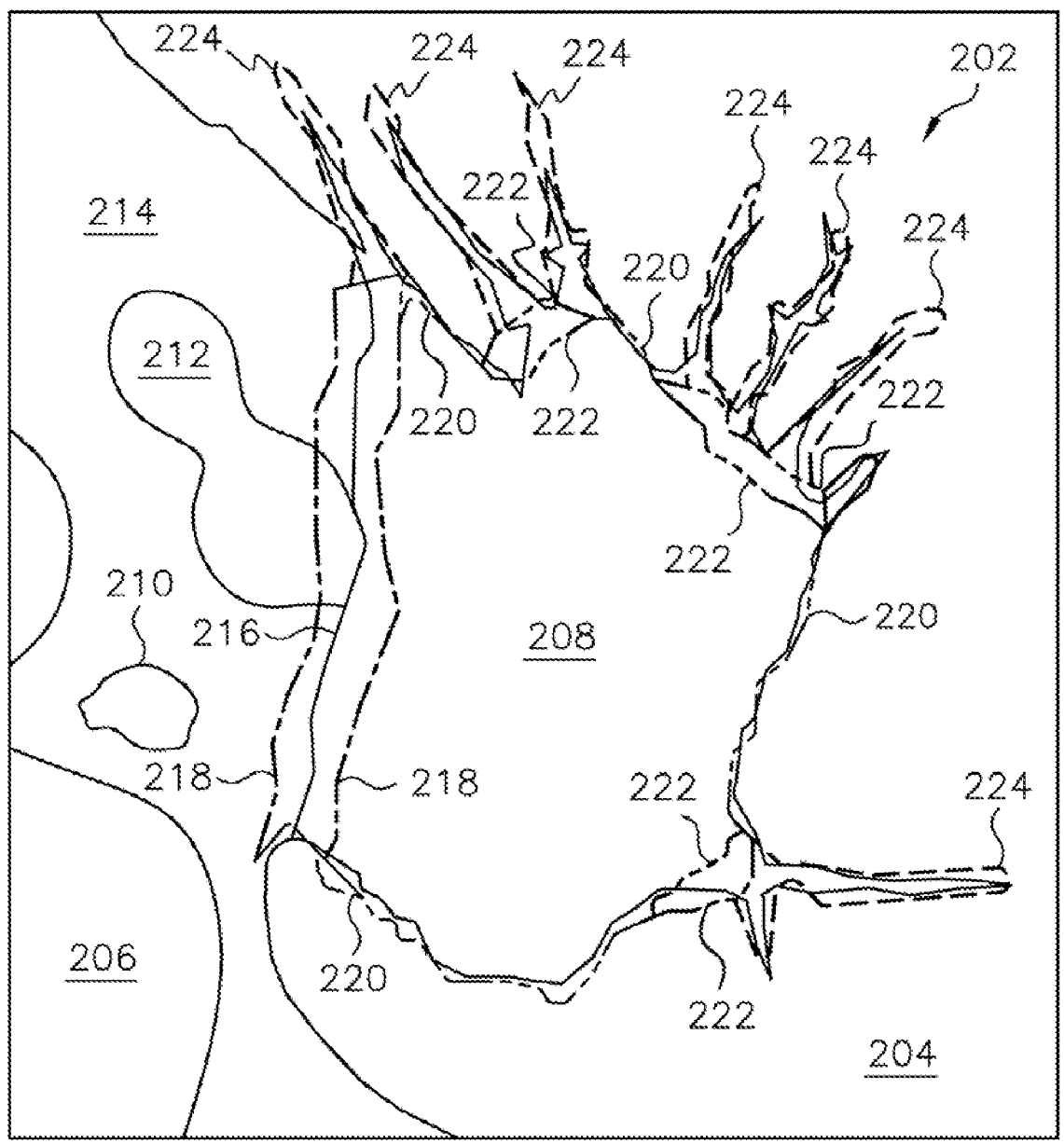
FIG. 6 schematically shows an alternate embodiment of a nodule boundary visualization method superimposed on a CT image.

Referring now to FIG. 4, a CT image slice through a large pulmonary nodule is shown. A CT image 214 shows a pulmonary nodule 202 comprising a mass substantially bounded within region 208 within lung portion 204. Other body features include a spinal portion 206 and other features 210 and 212 adjacent the lung. The pulmonary nodule 202 typically will include spicules that emanate from the nodule as best shown in FIG. 6. Those skilled in the art will understand that typical CT image often do not exhibit clearly defined boundaries for lesions such as nodules and surrounding features.

Figure 5:
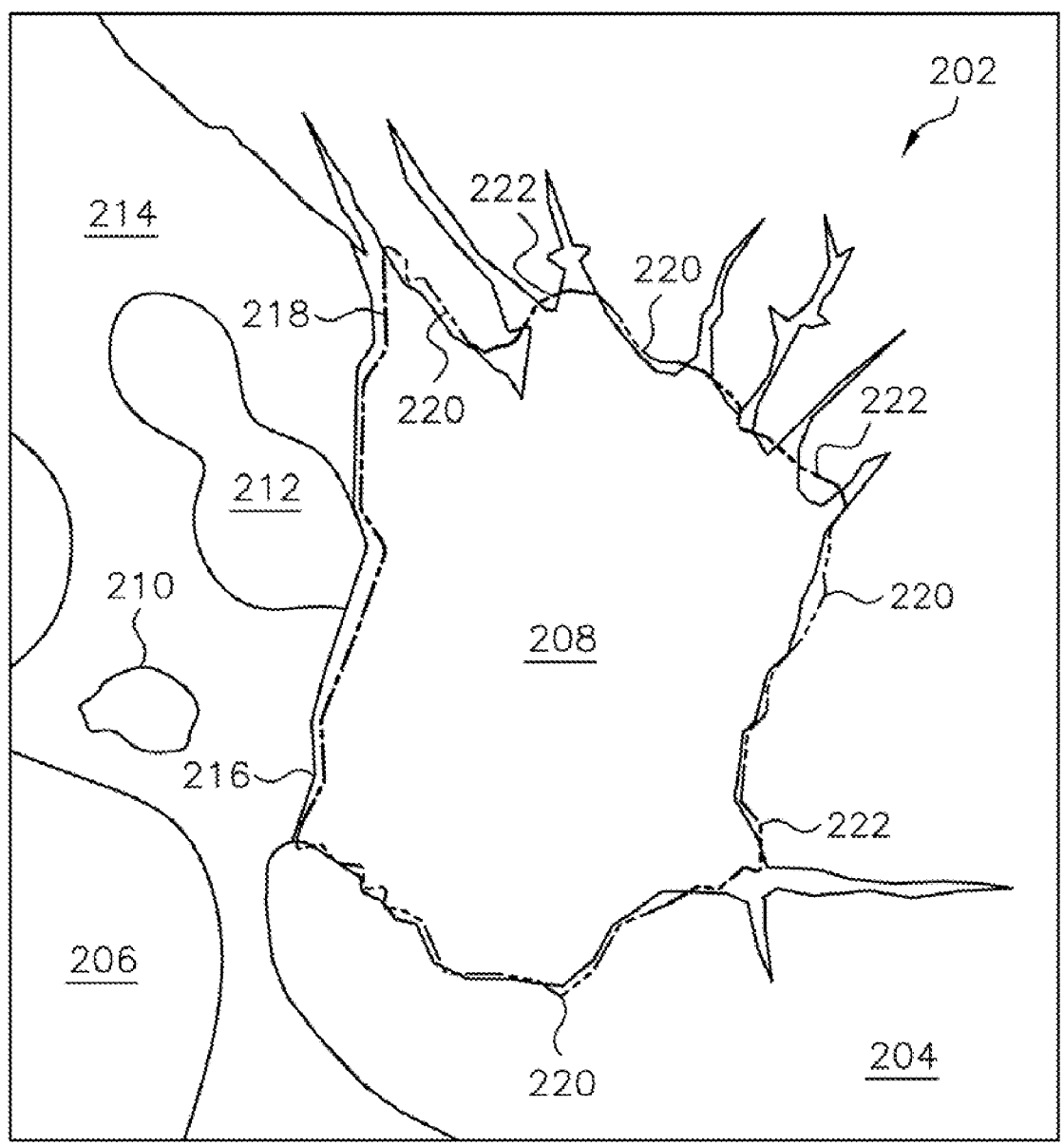
FIG. 5 schematically shows a nodule boundary visualization method superimposed on a CT image.

Referring now to FIG. 5, a nodule boundary visualization method is schematically shown superimposed on a CT image. In a preferred embodiment color-coded boundaries are represented by differing dashed lines 218, 220 and 222 indicate error source regions. In one example, dashed line 220 may correspond to a light green boundary indicating a region where there is a well-defined nodule margin, (e.g. having a high image gradient); therefore, the expected error of the green boundary will be small. Dashed line 222 may correspond to a light red boundary that indicates a region where the image gradient is low, or where there are small detailed features (called spicules) of the lesion that may be discarded from the volume estimation. The presence of either of a low image gradient or spicules will decrease measurement accuracy. Dashed line 2178 may correspond to a light blue boundary that indicates a region where there is little or no image gradient evidence of a boundary. For these situations at radiologist may be permitted as by interactive software to make a manual decision as to the location of the boundary. Areas exhibiting low image gradient provide the largest source of boundary location error. In this way, placement accuracy of a boundary of a nodule may be visualized to indicate the source of error and the potential size of the error.

In one embodiment of the invention color-coded boundaries may be automatically drawn on the display using known graphic software techniques in combination with information from the teachings herein. For example, colors may be selected based on the error associated with a given boundary as determined by edge-finding software and the associated error variance or other parameters as determined in accordance with the above teachings. Appropriate keys or legends may also be displayed to aid the operator in interpreting the display or images.

Referring now to FIG. 6, an alternate embodiment of a nodule boundary visualization method is schematically shown superimposed on a CT image. In the alternate embodiment the nodule may advantageously include colored boundary lines comprising, for example, yellow 224, light blue 218, light green 220 and light red 222, as colors are here indicated by dashed lines of varying types. Dual boundary lines encompassing the region 208 may be used to indicate the estimated bounds of error. That is, the true boundary of the nodule is expected to be located within the dual boundary lines. In this example, yellow 224 is used to outline fine detailed features, such as spicules, which are expected to be components of the nodule but are discarded in the measurement process with respect to the nodule volume calculation since they are also large sources of measurement error.

Such spicules include complex, but medically insignificant structures, that are treated statistically as outliers in accordance with the methods of the invention. Such structures tend to be long and thin, but have minute volume. In general, structures having small volume in relation to a high degree of error can be disconnected so as not to skew measurement accuracy results.

Figure 7B:
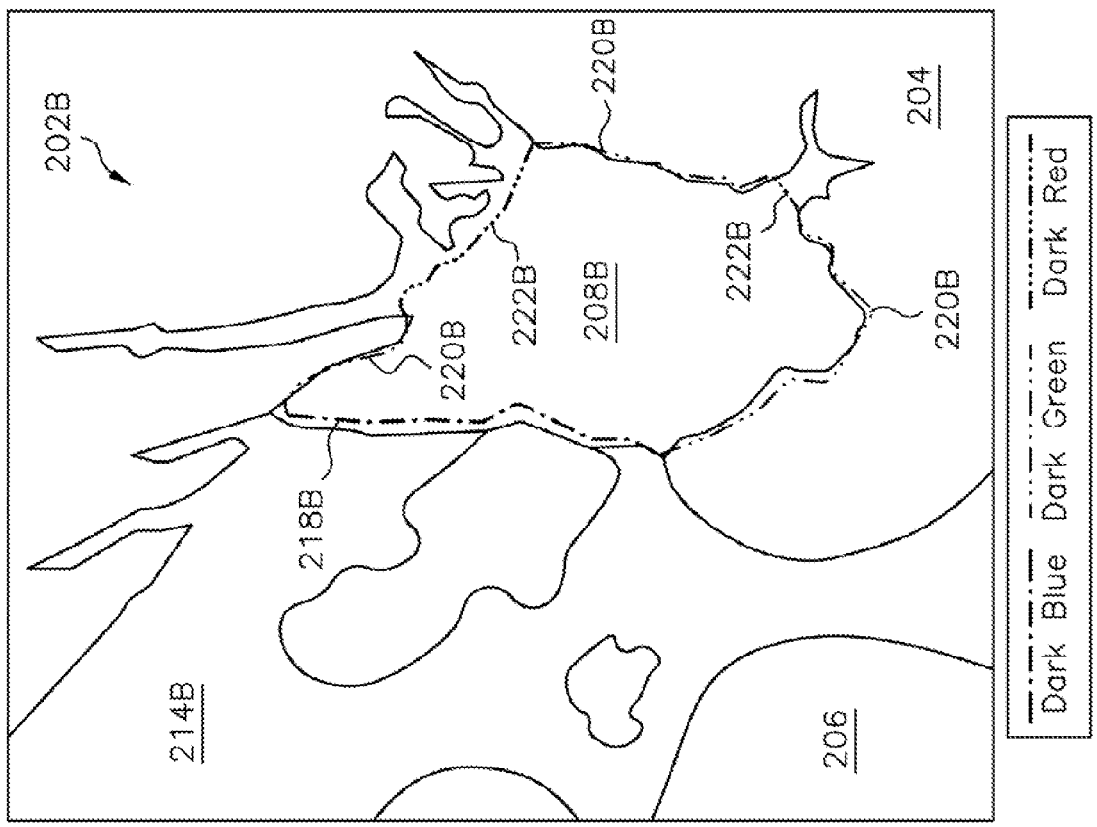
FIG. 7A and FIG. 7B schematically show an alternate embodiment of a module boundary visualization method superimposed on CT images acquired at different times.
Figure 7A:
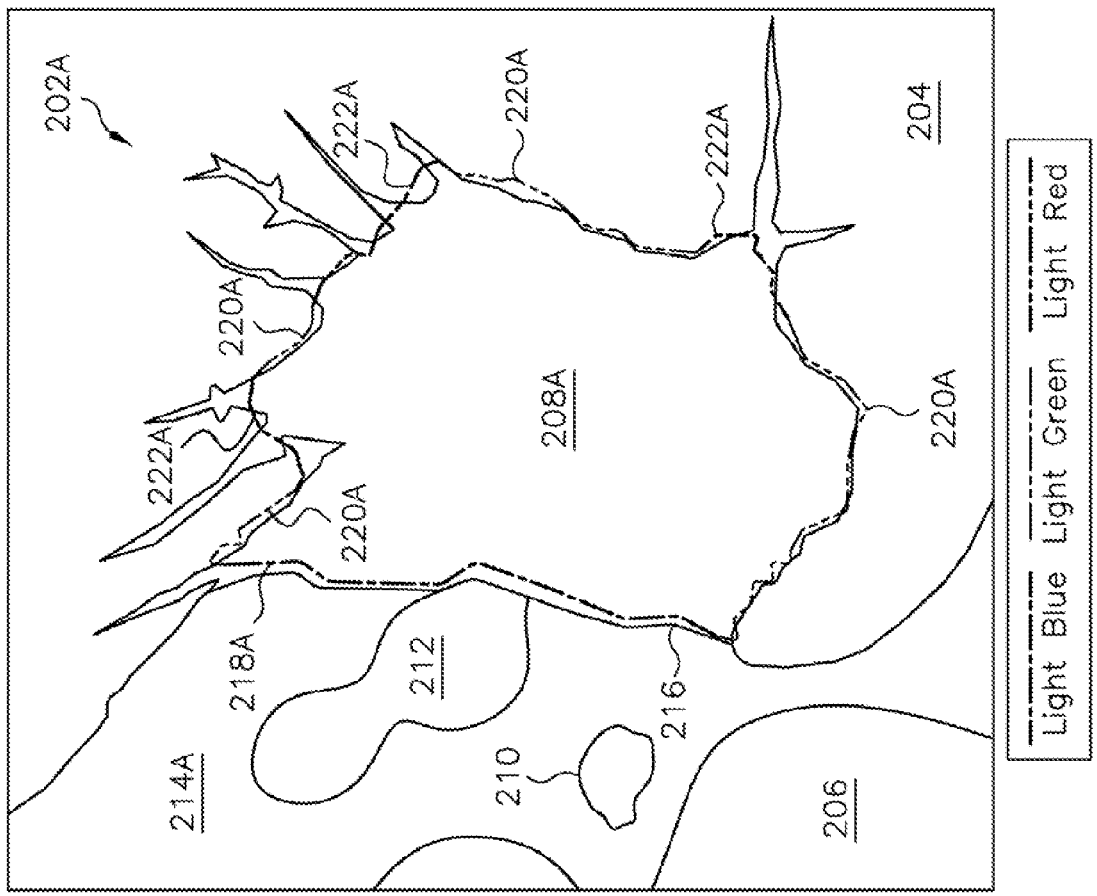

Referring now to FIG. 7A and FIG. 7B, an alternate embodiment of a nodule boundary visualization method is schematically shown superimposed on CT images acquired at different times. Here a visualization scheme similar to those described hereinabove may be used, where at lest two scans of a lesion are available and where the difference between the scans can also be visualized. FIG. 7A shows a first CT image 214A of a nodule 202A acquired at a first time and FIG. 7B shows a second CT image 214B of the same nodule 202B acquired at a second time. Color coded boundaries 218A, 220A, and 222A are applied to the first image 214A following the techniques described with reference to FIGS. 5 and 6 above. Color coded boundaries 218B, 220B, and 222B are applied to the second image 214B also following the techniques described with reference to FIGS. 5 and 6 above.

Referring now to FIG. 8A and FIG. 8B, another alternate embodiment of a nodule boundary visualization method is schematically shown superimposed on CT images acquired at different times showing one example in which the growth or other size change of a nodule may be visualized. Here boundaries 218A, 220A, and 222A from the first image are superimposed on boundaries 218B, 220B, and 222B obtained from the second image. The resulting overlays are displayed, as on a computer monitor or other suitable display, to provide a visualization of the change in nodule size as well as an indication of measurement accuracy corresponding to the color coded boundaries.

Those skilled in the art having the benefit of this disclosure will recognize that the boundary techniques described herein are not limited to the examples. There are many possible variations of the these visualization methods including:
1. Applying markings to 3-dimensional renderings of the nodule from all image slices,
2. Using transcluent (e.g. colored) markings so that the underlying structure can still be observed.
3. Using line shaded markings,
4. Using graduated markings so that distances can be quantitatively viewed,
5. Adding distance scale and text annotations so that quantitative measurements are presented, and/or
6. Any combination of the above.

Figure 9B:
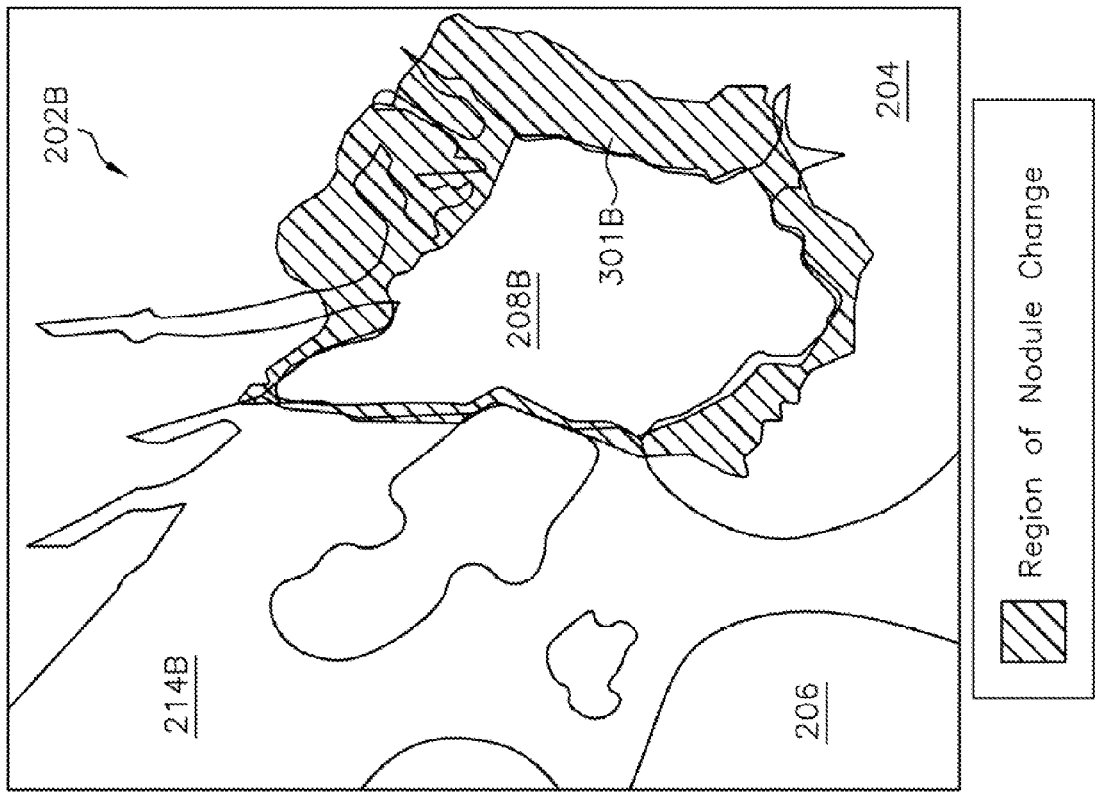
FIG. 9A and FIG. 9B schematically show another alternate embodiment of a nodule boundary visualization method superimposed on CT images acquired at different times.
Figure 9A:
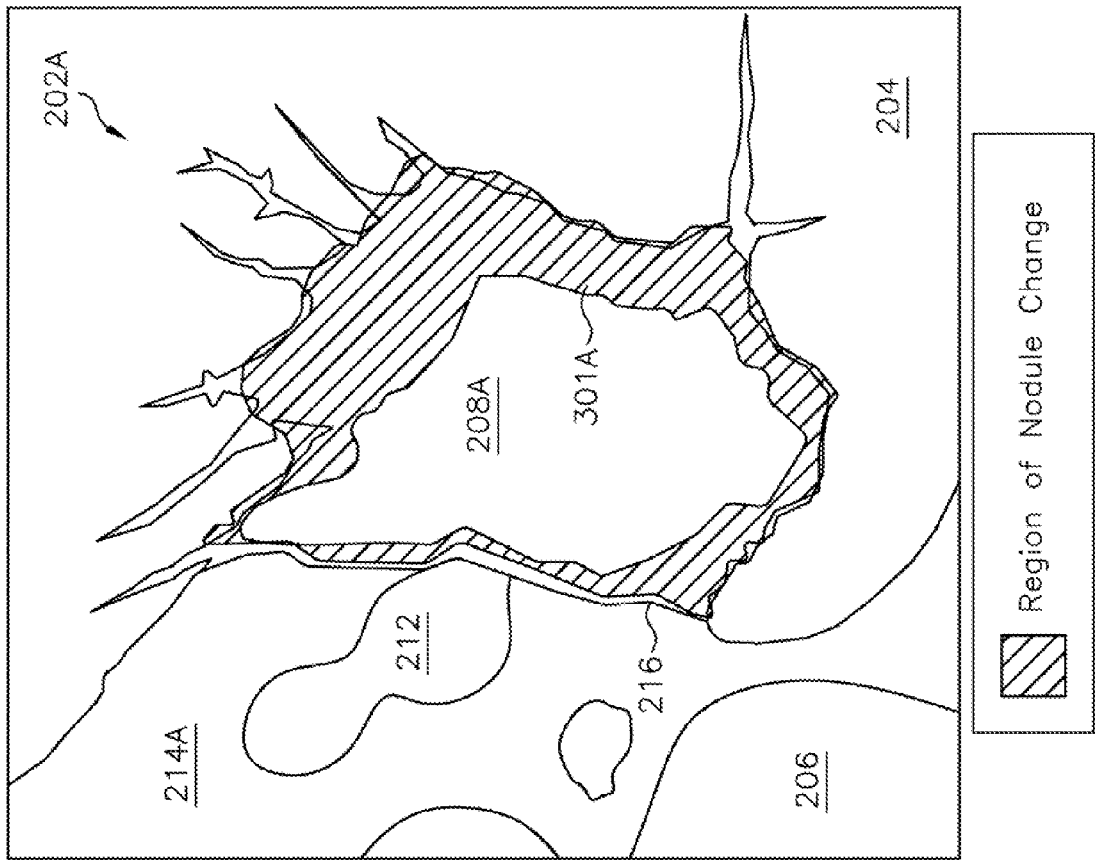

Referring now to FIG. 9A and FIG. 9B, another alternate embodiment of a nodule boundary visualization method is schematically shown superimposed on CT images acquired at different times showing another example in which the growth or other size change of a nodule may be visualized. Here the crosshatched areas 301A and 301B indicate the region of nodule size change between the two CT images 214A and 214B. The crosshatched area may advantageously be displayed on a color monitor as bright red, for example. Other colors may also be used.

Referring now to FIG. 10, another alternate embodiment of a nodule boundary visualization method is schematically shown superimposed on a CT image showing another example in which the growth or other size change of a nodule may be visualized. Here the various crosshatched areas 303, 305, 307 and 309 may be displayed as various colors to indicate change has occurred and with what degree of certainty. In one example, area 303 may correspond to a yellow region representing higher degree of change related to the original tumor size estimate. Area 307 may correspond to a green region relating to uncertainty in size related to the second measurement. Area 305 may correspond to a red region representing areas where there is a high probability of change. Area 309 may correspond to a blue region representing areas where an overlap in uncertain measurements occurs. This map also set a model for how we might want to measure response. Additionally a central point 320 may advantageously be selected so that an estimate of change can be made for various quadrants 320A, 320B, 320C and 320D of the mass. In some volumes, the change may be quite large compared to others, and the degree of certainty may also be different.

Referring now to FIG. 11, another alternate embodiment of a nodule boundary visualization method is schematically shown superimposed on a CT image showing yet another example in which the growth or other size change of a nodule may be visualized. FIG. 11 is substantially the same as FIG. 10 with the addition of boundary line 313 placed along that portion of the nodule where change cannot be reliably measured, but where no change can be reliably determined. This allows for the remainder of the nodule to be analyzed.

In yet another embodiment of the invention, an intervening chest scan may be taken in order to provide a prediction of tumor growth. The intervening chest scan may preferably be taken between a pre-treatment baseline scan and a post-treatment scan. In many cases the change in a tumor between the baseline scan and the intervening scan can be extrapolated to predict an expected change or growth in tumor size absent any treatment. For example, extrapolation of tumor growth may be done using a mathematical model based on exponential expected growth over time. The expected change can then be compared to an actual tumor size measurement in the post-treatment scan. Differences between the predicted growth size and the actual tumor size measurement can be used to make determinations regarding the effectiveness of treatment and the need for any revisions to the course of treatment. The process can be repeated as necessary for refining the course of treatment.

Using such an intervening scan, an error estimate can be applied to the growth rate. Using the error estimate and estimated growth rate, assumptions can be drawn about the potential effects of treatment on the growth rate. Confidence related to the growth rate estimate varies depending upon the time interval between the baseline scan and the intervening scan. A longer time period between scans or the faster tumor growth results in higher degrees of confidence.

In yet another aspect of the invention, a method for determining a bound on the range of error of an edge of a lesion includes the steps of:
collecting a database of known pathology images of lesions;
correlating each image in the database of known pathology images with a set of high resolution CT scan images of the same lesions by measuring and comparing CT boundary features of the set of high resolution CT scan images against known boundary features of the same lesions in the database to develop a set of edge range factors from the CT boundary features;
measuring boundary features in a CT scan image for a lesion of unknown pathology to create a set of unknown CT boundary features; and
comparing the set of unknown CT boundary features against the set of edge range factors to determine a range of an edge for the unknown CT boundary features.

In one example, at least one of the CT boundary features may be edge sharpness as represented in a high resolution CT scan image. Having developed the set of edge range factors from the CT boundary features of lesions of known pathology allows making a decision on the range of an edge for a lesion presenting the unknown CT boundary features with a higher degree of confidence in the decision.

Dynamic Intelligent Methods to Assist a User in Creating a Boundary Marking and in Estimating the Accuracy of That Marking The following describes extensions to the methods described hereinabove, the extended methods including automated or semi-automated methods for obtaining a minimum error boundary, and methods to dynamically visualize the error in a boundary, including the dynamic visualization for the automated methods. The methods are intended to be carried out by a user, such as a radiologist, interacting with computer software running on a processor, such as a personal computer.

Note, as used herein, a boundary may be a line in a two-dimensional image or a surface in a three dimensional or higher dimensional image. Image dimensions may be due to different image modalities. The algorithms used for boundary determination or boundary confidence estimation are not restricted to conventional two-dimensional image information but may employ evidence from a combination of multi-dimensional image information. Such multi-dimensional image information may be obtained from image color, three-dimensional image data, temporal image data, multi-modal image data, and/or problem domain information, such as a priori anatomical knowledge of the image region, or a priori probability information for the presence of a boundary.

One example of an automated marking method as employed by the present invention includes a two-phase process where in the first phase an automated boundary is created, and in the second phase the user iteratively modifies this boundary. An initial boundary is computed and marked on the image. There are a number of different ways that this boundary may be generated. For example, an anatomical a priori model may be matched to the image. One example of an a priori model is the left ventricle in an MRI dynamic cardiac image, other such image models may be used to good effect.

Another example of boundary generation drawings tools starts with the user marking a single point within the region of interest (ROI). A boundary image is then created by starting with the single marked point based on image features such as a pulmonary nodule in a CT image of the lung.

In yet another example, the user employs a region editing marking tool such as, for example, a circle, rectangle or freehand drawing tool, to surround the ROI. A software program running in a processor, such as a personal computer, finds an optimized boundary within the user-marked region. In yet another example, the user marks a point on the boundary of an object and a gradient-based search is employed in two opposite directions until an enclosed boundary is achieved. In still another example, the user marks at least two points on opposite sides of the ROI and the computer finds the best boundary in two different directions that links the at least two points. In still anther example, the user marks at least three points on the boundary of the ROI to create at least two point pairs and an optimized set of lines joining each of the at least two point pairs is automatically computed.

Once a boundary has been created by any of the methods described, it may be presented to the user for modification. The user can add additional points to the image through which a modified boundary should pass. Once the user has marked one or more modification points on the image a new boundary is computed that adapts to include the new points. This process may be repeated a number of times until the user is satisfied with the outcome.

Dynamic automatic extension of a user-marked boundary procedures assist the radiologist in marking a boundary by providing suggestions as to where the boundary is located. When a radiologist has marked a point or a part of a boundary and there exists evidence of a boundary, as by a high image gradient, the software program will extend that boundary while there is good consistent gradient evidence to do so. The resulting extended boundary is presented to the user for acceptance modification or rejection. The user may iteratively apply the method for dynamic automated extension. This boundary predicting method may incorporate any high-gradient boundary following algorithm, a number of which are known. When there are two marked boundary segments or boundary points, the method of the invention may advantageously employ a computer-run automated search method for connecting a boundary between two marked boundary segments or boundary points. After the search, a selection of boundary options may be offered to the user. The user may accept modify or reject any of the suggested boundaries.

Yet another embodiment of the invention automatically presents a visualization of the estimated error in a boundary using a confidence estimate marking. When any boundary is marked by the user or is automatically computed, each segment of the boundary may be marked with an automatically computed confidence estimate marking. The confidence estimate marking may be generated using a selected one or combination of two or more marking techniques including direct annotation, a boundary color, a widening of the marked boundary line, a boundary style visualization, or coloring/shading the image region adjacent to the boundary.

FIG. 12A-FIG. 12G illustrate one example of the use of drawing tools as employed by an imaging system constructed in accordance with one embodiment of the present invention. Referring now to FIG. 12A an original, unmarked image of a portion of a patient's chest cavity, including chest wall and lung parenchyma regions, is shown. In FIG. 12B a central point in a lesion as imaged by a CT scan is marked "X" by a user operating a computer marking tool, for example, FIG. 12C shows a partial boundary 1201 drawn automatically along a well-defined gradient, using a high-gradient boundary following algorithm. FIG. 12D shows a dotted line 1203 as may be manually started by a user to continue the boundary drawing process. 12E shows an automatic continuation 1205 of the dotted line 1203 introduced by the user. FIG. 12F shows another dotted line 1207, again introduced by the user. FIG. 12G shows another line 1210 automatically drawn to connect the previous user-drawn blue segment with the initial point "X," thereby completing a boundary around a lesion 1212.

FIG. 13A-FIG. 13D illustrate another example of the use of drawing tools as employed by an imaging system constructed in accordance with one embodiment of the present invention. FIG. 13A shows a plurality of seed points "X," placed by a user on an image of a portion of a patient's chest cavity, including chest wall and lung parenchyma regions and outlining a suspected lesion 1322. The lesion 1322 is characterized by a well defined boundary indicated by dashed lie 1312 and an indistinct boundary indicated by broken line 1314. FIG. 13B shows a first computer generated boundary 1316 automatically drawn using a computer operating a drawing program that is generated using the information in the image from the boundary lines and the plurality of user-placed seed points. FIG. 13C shows an example of user-placed seed point 1318, 1320 that may be added by the user after being presented with the automatically drawn first computer generated boundary 1316. FIG. 13D shows a final computer generated boundary 1320 that substantially defines the suspected lesion 1312. The final computer generated boundary 1320 is generated using the information in the image from the boundary lines, including the prior computer generated boundary line and the plurality of user-placed seed points.

FIG. 14A-FIG. 13D illustrate yet another example of the use of drawing tools as employed by a imaging system constructed in accordance with one embodiment of the present invention. FIG. 14A shows a plurality of seed points "X," placed by a user on a first image of a portion of a patient's chest cavity, including chest wall and lung parenchyma regions and outlining a suspected lesion 1422. The lesion 1422 is characterized by a boundary indicated by dashed line 1412 and an indistinct boundary indicated by broken line 1414. Also placed on the first image are computer marked boundary points "O."

Referring now to FIG. 14B, there shown is a second image of substantially the same portion of the same patient's lung cavity obtained at a later time. The user-placed boundary points "X" and computer marked boundary points "O" from the first image are copied and overlaid on the second image, where the second image shows a changed (larger in this example) suspected lesion 1422A characterized by boundary 1430.

Referring now to FIG. 14C, the overlaid user-placed boundary points "X" and computer marked boundary points "O" are translated to the boundary 1430 in the second image. FIG. 14D shows a final computer generated boundary 1432 that substantially defines the suspected lesion 1422A. The final computer generated boundary 1432 is generated using the information in the image from the boundary lines, including the prior computer generated boundary line and the plurality of user-placed and computer marked boundary points.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An automated method for determining a bound on the error of a size change measurement, the method comprising the steps of:
   scanning a body part with an imaging system to produce a first set of imaging data;
   identifying at least one target lesion in the imaging data;
   rescanning the body part so as to produce a second set of imaging data;
   identifying the at least one target lesion in the second set of imaging data;
   measuring the at least one target lesion as imaged in both the first set of imaging data and the second set of imaging data to determine a first apparent target lesion size corresponding to the first set of imaging data and a second apparent target lesion size corresponding to the second set of imaging data; estimating a change in size by comparing the first and second apparent lesion sizes; and
   estimating a variance where the variance includes a set of variance measurements from a plurality of factors selected from the group consisting of nodule form, scanner parameters, patient factors, algorithm factors, operator factors, nodule tissue, scanner point spread function, patient motion, features of the at least one target lesion, features of adjacent structures, features of the imaging system including its inherent resolution, and noise present in the image so as to determine a bound on the change in size measurement.

2. The method of claim 1 wherein the size measurements comprise at least one size measurement selected from the group consisting of length, area and three-dimensional volume of the lesion.

3. The method of claim 1 further comprising the step of defining the edge of the at least one target lesion by adjusting the apparent image volume for the at least one target lesion according to the estimated variance to produce at least two adjusted image volumes.

4. The method of claim 3 wherein the step of defining the edge of the at least one target lesion further comprises the step of applying a threshold and/or a gradient function to the at least one target lesion to determine the boundary for the edge.

5. The method of claim 1 wherein each step is carried out by software that allows for interaction of a medical professional.

6. The method of claim 1 further including the step of automatically estimating a degree of motion for a particular structure.

7. The method of claim 6 wherein the step of automatically estimating a degree of motion for a particular structure includes measuring a degree of variation of surface structures and structures outside of the target lesion.

8. The method of claim 1 further comprising the step of automatically matching corresponding images of the at least one target lesion acquired at differing times.

9. The method of claim 8 further comprising the step of selecting the at least one target lesion as an object having a maximal area, maximal length or maximal volume and finding a comparable object obtained at a subsequent time.

10. The method of claim 1 further including the step of spatially calibrating an imaging system using at least one phantom and measuring quantities selected from the group consisting of bias, reproducibility, noise, scanner artifacts and image distortion.

11. The method of claim 10 wherein the step of spatially calibrating further includes the step of conducting phantom studies to establish maps that characterize the degree of noise, scanner artifacts and image distortion for all pertinent regions of the human body for a given scanner; and using the maps to determine a bound for the measurement error of the measurement of the target lesion.

12. The method of claim 1 wherein the body part is a lung further comprising the step of automatically segmenting other lung features from the at least one target lesion.

13. The method of claim 1 wherein the imaging system is selected from the group consisting of a computerized tomography scanner, magnetic resonance imager, positron emission imaging system, X-ray imaging system, vascular interventional and angiogram/angiography procedures, and an ultrasound imaging system.

14. The method of claim 1 further including the step of using a calibration device during scanning.

15. The method of claim 14 wherein the calibration device comprises a synthetic phantom.

16. The method of claim 14 wherein the calibration device comprises a set of synthetic phantoms of varying size.

17. The method of claim 14 wherein the calibration device is selected from the group consisting of wires, beads, rods and geometrical shapes.

18. The method of claim 14 wherein the calibration device is an in vivo device.

19. The method of claim 18 wherein the in vivo device is selected from the group consisting of wires, beads, catheters, implantable devices and items of known dimensions in the patient's body.

20. An automated method for determining a bound on the error of a size change measurement, the method comprising the steps of:
- scanning a body part with an imaging system to produce a first set of imaging data;
- identifying a plurality of target lesions in the imaging data;
- rescanning the body part so as to produce a second set of imaging data;
- identifying the plurality of target lesions in the second set of imaging data;
- measuring the plurality of target lesions as imaged in both the first set of imaging data and the second set of imaging data to determine a first apparent target lesion value corresponding to the first set of imaging data and a second apparent target lesion value corresponding to the second set of imaging data;
- estimating a change in target lesion value by comparing the first and second apparent lesion values; and
- estimating a variance so as to determine a bound on the change in value measurement where the variance includes a set of variance measurements from a plurality of factors selected from the group consisting of nodule form, scanner parameters, patient factors, algorithm factors, operator factors, nodule tissue, scanner point spread function, patient motion, features of the at least one target lesion, features of adjacent structures, features of the imaging system including its inherent resolution, and noise present in the image.

21. The method of claim 20 wherein at least one target lesion value is smaller than 1 cm.

* * * * *